US008609287B2

(12) United States Patent
Zhang et al.

(10) Patent No.: US 8,609,287 B2
(45) Date of Patent: Dec. 17, 2013

(54) POLYETHER-FUNCTIONALIZED REDOX SHUTTLE ADDITIVES FOR LITHIUM ION BATTERIES

(75) Inventors: Zhengcheng Zhang, Naperville, IL (US); Lu Zhang, Lisle, IL (US); Khalil Amine, Oak Brook, IL (US)

(73) Assignee: Uchicago Argonne, LLC, Chicago, IL (US)

( * ) Notice: Subject to any disclaimer, the term of this patent is extended or adjusted under 35 U.S.C. 154(b) by 172 days.

(21) Appl. No.: 13/114,452

(22) Filed: May 24, 2011

(65) Prior Publication Data

US 2011/0294003 A1 Dec. 1, 2011

Related U.S. Application Data

(60) Provisional application No. 61/348,063, filed on May 25, 2010.

(51) Int. Cl.
*H01M 6/16* (2006.01)

(52) U.S. Cl.
USPC ........... 429/336; 429/234; 429/235; 429/341; 568/608

(58) Field of Classification Search
None
See application file for complete search history.

(56) References Cited

U.S. PATENT DOCUMENTS

| | | | | |
|---|---|---|---|---|
| 5,441,862 | A * | 8/1995 | Weber et al. | 430/551 |
| 5,526,599 | A | 6/1996 | Roussel | |
| 5,709,968 | A | 1/1998 | Shimizu | |
| 5,763,119 | A | 6/1998 | Adachi | |
| 5,858,324 | A | 1/1999 | Dahn et al. | |
| 5,858,573 | A | 1/1999 | Abraham et al. | |
| 5,882,812 | A | 3/1999 | Visco et al. | |
| 5,900,385 | A | 5/1999 | Dahn et al. | |
| 6,004,698 | A | 12/1999 | Richardson et al. | |
| 6,045,952 | A | 4/2000 | Kerr et al. | |
| 6,143,268 | A | 11/2000 | Dahn et al. | |
| 6,203,944 | B1 | 3/2001 | Turner et al. | |
| 6,255,017 | B1 | 7/2001 | Turner | |
| 6,387,571 | B1 | 5/2002 | Lain et al. | |
| 6,436,578 | B2 | 8/2002 | Turner et al. | |
| 6,503,662 | B1 | 1/2003 | Hamamoto et al. | |
| 6,664,004 | B2 | 12/2003 | Krause et al. | |
| 6,680,145 | B2 | 1/2004 | Obrovac et al. | |
| 6,699,336 | B2 | 3/2004 | Turner et al. | |
| 6,964,828 | B2 | 11/2005 | Lu et al. | |
| 7,078,128 | B2 | 7/2006 | Lu et al. | |
| 7,211,237 | B2 | 5/2007 | Eberman et al. | |
| 7,507,503 | B2 | 3/2009 | Amine et al. | |
| 7,618,749 | B2 | 11/2009 | Kim et al. | |
| 7,648,801 | B2 | 1/2010 | Dahn et al. | |
| 7,968,235 | B2 | 6/2011 | Amine et al. | |
| 2003/0027048 | A1 | 2/2003 | Lu et al. | |
| 2003/0211390 | A1 | 11/2003 | Dahn et al. | |
| 2004/0121234 | A1 | 6/2004 | Le | |
| 2004/0121239 | A1 | 6/2004 | Abe et al. | |
| 2004/0131936 | A1 | 7/2004 | Turner et al. | |
| 2004/0179993 | A1 | 9/2004 | Dahn et al. | |
| 2005/0019670 | A1 | 1/2005 | Amine et al. | |
| 2005/0031957 | A1 | 2/2005 | Christensen et al. | |
| 2005/0221168 | A1 | 10/2005 | Dahn et al. | |
| 2005/0221196 | A1 | 10/2005 | Dahn et al. | |
| 2006/0045144 | A1 | 3/2006 | Karlsen et al. | |
| 2006/0046144 | A1 | 3/2006 | Obrovac | |
| 2006/0199080 | A1 | 9/2006 | Amine et al. | |
| 2006/0263695 | A1 | 11/2006 | Dahn et al. | |
| 2007/0072085 | A1 | 3/2007 | Chen et al. | |
| 2007/0212614 | A1 | 9/2007 | Kim et al. | |
| 2009/0286162 | A1 | 11/2009 | Lamanna et al. | |

FOREIGN PATENT DOCUMENTS

| | | |
|---|---|---|
| JP | 06-338347 | 12/1994 |
| JP | 07-191442 | 7/1995 |
| JP | 07-302614 | 11/1995 |
| JP | 2000-058117 | 2/2000 |
| JP | 2002-260730 | 9/2002 |
| JP | 2004-063112 | 2/2004 |
| JP | 2004-234948 | 8/2004 |
| JP | 2004-349132 | 12/2004 |
| WO | WO-01/29920 | 4/2001 |

OTHER PUBLICATIONS

Jayakannan, M.; Ramakrishnan, S., Segmented polyethylene oxides: a new class of polyethers prepared via melt transetherification, Journal of Polymer Science, Part A: Polymer Chemistry (2001), 39 (10), 1615-1628.*
Chen, J. et al., "Chemical Overcharge and Overdischarge Protection for Lithium-Ion Batteries," Electrochemical and Solid-State Letters, 8 (1), pp. A59-A62, (2005), published by The Electrochemical Society, Inc.
Chen, Z. et al., "Bifunctional Electrolyte Additive for Lithium-Ion Batteries", Electrochemistry Communications, 9, (2007), pp. 703-707.
Chen, Z. et al., "Redox Shuttles for Safer Lithium-Ion Batteries", Electrochimica Acta 54 (2009) pp. 5605-5613.
Chen, Z. et al., "Understanding the Stability of Aromatic Redox Shuttles for Overcharge Protection of Lithium-Ion Cells," Joumal of Electrochemical Society, 153, 2006, A2215-A2219.
Moshurchak, L.M. et al., "High-Potential Redox Shuttle for Use in Lithium-Ion Batteries", Journal of The Electrochemical Society, 156, (4), (2009), pp. A309-A312.
International Search Report and Written Opinion of the International Searching Authority for PCT/US2011/037782 issued Jan. 11, 2012 (12 pages).
Office Action in Japanese Application No. 2013-510370 dtd Jun. 28, 2013. (with English translation).
Office Action (with English translation) issued for Japanese Application No. 2013-510370 dated Apr. 12, 2013.
Final Notice of Reasons for Rejection in Japanese Application No. 2013-510370 dated Sep. 4, 2013 (English translation).

* cited by examiner

*Primary Examiner* — Cynthia K. Walls
(74) *Attorney, Agent, or Firm* — Foley & Lardner LLP

(57) ABSTRACT

Compounds may have general Formula I, II, or III:

I

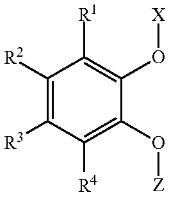

-continued

II

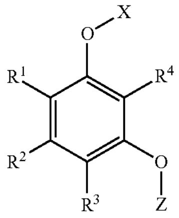

III

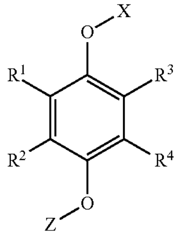

where $R^1$, $R^2$, $R^3$, and $R^4$ are independently H, F, Cl, Br, CN, $NO_2$, a alkyl group, a haloalkyl group, a phosphate group, a polyether group; or $R^1$ and $R^2$, or $R^3$ and $R^4$, or $R^2$ and $R^3$ (in the case of Formula II) may join together to form a fused ring on the benzene ring; and X and Z are independently a group of Formula A:

A

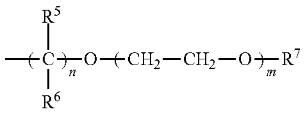

where $R^5$ and $R^6$ and $R^7$ are independently H, F, Cl, Br, CN, $NO_2$, a alkyl group, a haloalkyl group, a phosphate group, or a polyether group; $R^7$ is H, F, Cl, Br, CN, $NO_2$, a alkyl group, a haloalkyl group, a phosphate group, or a polyether group; n is an integer from 1 to 8; and m is an integer from 1 to 13. Such compounds may be used as redox shuttles in electrolytes for use in electrochemical cells, batteries and electronic devices.

21 Claims, 11 Drawing Sheets

POLYETHER-FUNCTIONALIZED REDOX SHUTTLE ADDITIVES FOR LITHIUM ION BATTERIES

CROSS-REFERENCE TO RELATED APPLICATIONS

This application claims the benefit of U.S. Provisional Patent Application 61/348,063, filed on May 25, 2010, the entire contents of which are incorporated herein by reference, for any and all purposes.

GOVERNMENT INTERESTS

The United States Government has rights in this invention pursuant to Contract No. DE-AC02-06CH11357 between the United States Government and UChicago Argonne, LLC, representing Argonne National Laboratory.

FIELD

The present technology relates generally to the electrolyte redox shuttle compounds carried in the non-aqueous electrolyte providing intrinsic overcharge protection capability for lithium ion batteries, electrical double-layer capacitors and other electrochemical devices.

BACKGROUND

Lithium ion batteries were first commercialized in 1990, and soon thereafter drew tremendous attention from academic and industry interests due to the advantages such as high energy density and rapid charge/discharge capabilities in comparison to state of the battery technology at the time. In recent years, lithium ion battery technology has become the most popular power source for portable electronic devices. In addition, lithium ion batteries have found application in hybrid electric vehicles (HEV) and plug-in hybrid electric vehicles (PHEV). However, safety of lithium batteries continues to plague the technology. For example, secondary lithium-ion batteries are known to exhibit problems in shorting of the battery, elevated operating temperatures and overcharge, which can lead to dangerous situations such as overheating, fire, and explosion of the battery.

Overcharge occurs when electricity flow is forced through a cell when its capacity is already full. This is one of the most common factors that could lead to serious safety issues of lithium-ion batteries. Due to the manufacture processes, there is always a "weakest cell" in a battery pack (i.e. the cell with the lowest charging capability in a multi-cell battery pack). During charging, the weakest cell will reach full capacity prior to the other cells, but because the overall voltage of the battery is not high, the full capacity cell with not trigger the voltage monitor of the charger to read "full." As a result, the weakest cell is put into an overcharge situation. Instead of being stored evenly across all electrodes in the battery pack, electricity will build up in, and increase the potential of, the cathode in the weakest cell, causing the potential to go beyond the electrochemical window of the electrolyte. In turn, this will cause reactions to occur such as oxidation of the electrolyte, leading up to and including explosion of the cell and battery pack.

Known methods to avoid the overcharge abuse in practice, include the use of electronic devices attached to each individual cell to monitor for overcharge, the use of overcharge protection compounds in each cell, and the use of redox shuttles in the electrolyte of the electrochemical cells.

A number of redox shuttle compounds are known. Generally, the redox shuttle molecule can be reversibly oxidized and reduced at a defined potential slightly higher than the end-of-charge potential of the positive electrode. This mechanism can protect the cell from overcharge by locking the potential of the positive electrode at the oxidation potential of the shuttle molecules.

For an ideal redox shuttle compound, there are at least three desirable properties. The first property is that it should have a reversible oxidation potential that is appropriate for the cathode material with which it is to be used. This means that the oxidation potential of the redox shuttle should be between 0.3V and 0.5V volts higher than the end-of-charge potential of the cathode. This will ensure that redox shuttle is accessed only overcharge potentials. The second property is that the redox shuttle should be electrochemically stabile or reversible. The stability and reversibility of the redox shuttle will determine how much overcharge protection is provided. The third property is that the redox shuttle is to have sufficient solubility in the electrolyte system in order to have an effective amount of the redox shuttle available.

SUMMARY

In one aspect, a compound of Formula I, II, or III is provided:

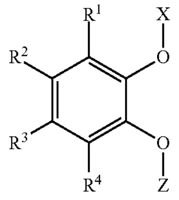

I

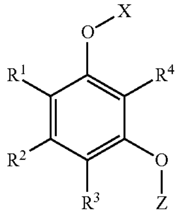

II

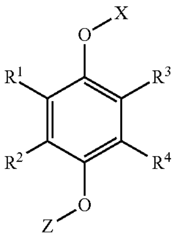

III where $R^1$, $R^2$, $R^3$, and $R^4$ are independently H, F, Cl, Br, CN, $NO_2$, a alkyl group, a haloalkyl group, a phosphate group, a polyether group; or $R^1$ and $R^2$, or $R^3$ and $R^4$, or in the case of Formula II $R^2$ and $R^3$ may join together to form a fused ring on the benzene ring; and X and Z are independently a group of Formula A:

A

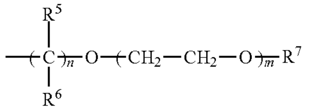

where $R^5$ and $R^6$ are independently H, F, Cl, Br, CN, $NO_2$, a alkyl group, a haloalkyl group, a phosphate group, or a polyether group; $R^7$ is H, a alkyl group, a haloalkyl group, a phosphate group, or a polyether group; n is an integer from 1 to 8; and m is an integer from 1 to 13. In some embodiments, $R^1$, $R^2$, $R^3$, and $R^4$ are independently H, a alkyl group, a haloalkyl group, or a polyether group. In some embodiments, $R^1$, $R^2$, $R^3$, and $R^4$ are independently H, a $C_1$-$C_4$ alkyl group, a $C_1$-$C_4$ haloalkyl group, or a polyether group having from 2 to 20 carbon atoms. In some embodiments, $R^1$ and $R^4$ are the same and are different from that of $R^2$ and $R^3$. In some embodiments, $R^1$ and $R^4$ are individually an alkyl group or a haloalkyl group, and $R^2$ and $R^3$ are hydrogen. In some embodiments, $R^1$ and $R^4$ are individually methyl, ethyl, n-propyl, iso-propyl, n-butyl, sec-butyl, or tert-butyl and $R^2$ and $R^3$ are H. In some embodiments, n is 1 to 3. In some embodiments, m is from 1 to 6.

In some embodiments, $R^5$ and $R^6$ at each occurrence are individually H, a $C_1$-$C_4$ alkyl, a $C_1$-$C_4$ haloalkyl, H, Cl, Br, or I. In some embodiments, $R^5$ and $R^6$ are H, methyl, ethyl, n-propyl, iso-propyl, n-butyl, sec-butyl, or tert-butyl. In some embodiments, $R^7$ is H or an alkyl group. In some embodiments, $R^7$ is H or a $C_1$-$C_4$ alkyl group. In some embodiments, $R^7$ is H, methyl, ethyl, n-propyl, iso-propyl, n-butyl, sec-butyl, or tert-butyl. In some embodiments, n is 1 or 2. In some embodiments, n is 2. In some embodiments, m is 1, 2, 3, or 4.

In some embodiments, the compound is that of Formula I; $R^1$, $R^2$, $R^3$, and $R^4$ are independently H, a $C_1$-$C_4$ alkyl group, a $C_1$-$C_4$ haloalkyl group, or a polyether group having from 2 to 20 carbon atoms; $R^5$ and $R^6$ at each occurrence are individually H, a $C_1$-$C_4$ alkyl, a $C_1$-$C_4$ haloalkyl, H, Cl, Br, or I; and $R^7$ is H or an alkyl group. In some embodiments, the compound is that of Formula I; $R^1$, $R^2$, $R^3$, and $R^4$ are independently H, methyl, ethyl, n-propyl, iso-propyl, n-butyl, sec-butyl, or tert-butyl, or a polyether group having from 2 to 20 carbon atoms; $R^5$ and $R^6$ at each occurrence are individually H or methyl; $R^7$ is H, methyl, ethyl, n-propyl, iso-propyl, n-butyl, sec-butyl, or tert-butyl; and n is 1 or 2. In some embodiments, the compound is that of Formula I; $R^1$ and $R^4$ are the same and are different from that of $R^2$ and $R^3$; $R^5$ and $R^6$ at each occurrence are individually H, a $C_1$-$C_4$ alkyl, a $C_1$-$C_4$ haloalkyl, H, Cl, Br, or I; $R^7$ is H or an alkyl group; and n is 1 or 2. In some embodiments, the compound is that of Formula I; $R^1$ and $R^4$ are individually an alkyl group or a haloalkyl group; $R^2$ and $R^3$ are hydrogen; $R^5$ and $R^6$ at each occurrence are individually H or methyl; $R^7$ is H, methyl, ethyl, n-propyl, iso-propyl, n-butyl, sec-butyl, or tert-butyl; and n is 1 or 2. In some embodiments, the compound is that of Formula I; $R^1$ and $R^4$ are tert-butyl; $R^2$ and $R^3$ are H; $R^5$ and $R^6$ at each occurrence are individually H or methyl; $R^7$ is H, methyl, or ethyl; and n is 1 or 2. In such embodiments, m is from 1 to 10. In other such embodiments, m is from 1 to 6.

In some embodiments, the compound is 1-nitro-3-tert-butyl-2,5-di-oligo(ethylene glycol)benzene; 1-cyano-3-tert-butyl-2,5-di-oligo(ethylene glycol)benzene; 1,4-di-tert-butyl-2,3-di-oligo(ethylene glycol)benzene; 5-tert-butyl-1,3-dinitro-2,4-di-oligo(ethylene glycol)benzene; 1-(benzyloxy)-4-bromo-2,3-di-oligo(ethylene glycol)benzene; 1,3,5-tri-tert-butyl-2,4-di-oligo(ethylene glycol)benzene; 2-methyl-1,4-di-oligo(ethylene glycol)benzene; 2,3-dimethyl-1,4-di-oligo(ethylene glycol)benzene; 2,5-dimethyl-1,4-di-oligo(ethylene glycol)benzene; 2,6-dimethyl-1,4-di-oligo(ethylene glycol)benzene; 2,3,6-trimethyl-1,2-di-oligo(ethylene glycol)benzene; 2,3,5,6-tetramethyl-1,4-di-oligo(ethylene glycol)benzene; 4-methyl-1,2-di-oligo(ethylene glycol)benzene; 2,3,5,6-tetramethyl-1,4-di-oligo(ethylene glycol)benzene; 2-ethyl-1,4-di-oligo(ethylene glycol)benzene; 2,3-diethyl-1,4-di-oligo(ethylene glycol)benzene; 2,5-diethyl-1,4-di-oligo(ethylene glycol) benzene; 2,6-diethyl-1,4-di-oligo(ethylene glycol)benzene; 2,3,6-triethyl-1,2-di-oligo(ethylene glycol)benzene; 2,3,5,6-tetraethyl-1,4-di-oligo(ethylene glycol)benzene; 4-ethyl-1,2-di-oligo(ethylene glycol)benzene; 2,5-diisopropyl-1,4-di-oligo(ethylene glycol)benzene; 2-tert-butyl-1,4-di-oligo (ethylene glycol)benzene; 2,3-di-tert-butyl-1,4-di-oligo (ethylene glycol)benzene; 2,5-di-tert-butyl-1,4-di-oligo (ethylene glycol)benzene; 2,5-di-tert-pentyl-1,4-di-oligo (ethylene glycol)benzene; 2,5-di-tert-butyl-3,6-di-nitro-1,4-di-oligo(ethylene glycol)benzene; 2,5-di-tert-butyl-3,6-di-cyano-1,4-di-oligo(ethylene glycol)benzene; 2,5-di-tert-butyl-1,4-di-oligo(ethylene glycol)benzene; 2,5-dicyclohexyl-1,4-di-oligo(ethylene glycol)benzene; 4-tert-butyl-1,2-di-oligo(ethylene glycol)benzene; 4,5-di-tert-butyl-1,2-di-oligo(ethylene glycol)benzene; 4,5-di-tert-pentyl-1,2-di-oligo(ethylene glycol)benzene; 4,5-di-tert-butyl-1,2-diethoxybenzene; 9,10-di-oligo(ethylene glycol)-1,4:5,8-dimethano-1,2,3,4,5,6,7,8-octahydroanthracene; 9,10-di-oligo(ethylene glycol)-1,4:5,8-diethano-1,2,3,4,5,6,7,8-octahydroanthracene; 1,4-bis(2-methoxy)ethoxy-2,5-di-tert-butyl-benzene; 1,4-bis(2-(2-methoxy)ethoxy)ethoxy-2,5-di-tert-butyl-benzene; 1,4-bis(2-(2-(2-methoxy)ethoxy) ethoxy)ethoxy-2,5-di-tert-butyl-benzene; or 1,4-bis(2-(2-(2-(2-methoxy)ethoxy)ethoxy)ethoxy)ethoxy-2,5-di-tert-butyl-benzene.

In some embodiments, the compound is 1,4-bis(2-methoxy)ethoxy-2,5-di-tert-butyl-benzene; 1,4-bis(2-(2-methoxy)ethoxy)ethoxy-2,5-di-tert-butyl-benzene; 1,4-bis(2-(2-(2-methoxy)ethoxy)ethoxy)ethoxy-2,5-di-tert-butyl-benzene; or 1,4-bis(2-(2-(2-(2-methoxy)ethoxy)ethoxy) ethoxy)ethoxy-2,5-di-tert-butyl-benzene.

In another aspect, an electrolyte is provided including an alkali metal salt; a polar aprotic solvent; and a redox shuttle, where the redox shuttle is any of compounds of Formula I, II, or III described above generally, or specifically, and where the electrolyte solution is substantially non-aqueous. In some embodiments, the redox shuttle has a redox potential of from 3 V to 5 V in the electrolyte. In some embodiments, the redox shuttle is present in the electrolyte from 0.0005 wt % to 50 wt %. In some embodiments, the redox shuttle is present in the electrolyte from 2 wt % to 10 wt %.

In some embodiments, the electrolyte also includes an electrode stabilizing compound that can be reduced or polymerized on the surface of a negative electrode to form a passivation film on the surface of negative electrode. In other embodiments, the electrolyte also includes an electrode stabilizing compound that can be oxidized or polymerized on the surface of positive electrode to form a passivation film on the surface of the positive electrode. In some embodiments, the electrode stabilizing compound is present from 0.001 wt % to 8 wt %.

In some embodiments, the alkali metal salt is other than $Li[B(C_2O_4)_2]$ or $Li[BF_2(C_2O_4)]$, and the electrolyte further includes an electrode stabilizing compound that is $Li[B(C_2O_4)_2]$ or $Li[BF_2(C_2O_4)]$. In some embodiments, the electrode stabilizing compound is present from 0.001 wt % to 8 wt %.

In another aspect, an electrochemical device is provided including a cathode; an anode; and an electrolyte including an alkali metal salt, a polar aprotic solvent, and a redox shuttle that is compound of Formula I, II, or III, as described above, where the electrolyte solution is substantially non-aqueous. In some embodiments, the device is a lithium secondary battery; the cathode is a lithium metal oxide cathode; the anode is a carbon, a lithium metal anode, or a lithium alloy; and the anode and cathode are separated from each other by a porous separator. In some embodiments, the cathode includes a spinel, a olivine, a carbon-coated olivine, $LiFePO_4$, $LiCoO_2$, $LiNiO_2$, $LiNi_{1-x}Co_yMet_zO_2$, $LiMn_{0.5}Ni_{0.5}O_2$, $LiMn_{0.3}Co_{0.3}Ni_{0.3}O_2$, $LiMn_2O_4$, $LiFeO_2$, $LiMet_{0.5}Mn_{1.5}O_4$, $Li_{1+x'}Ni_\alpha Mn_\beta Co_\gamma Met'_\delta O_{2-z'}F_{z'}$, Nasicon, $A_{n'}B_2(XO_4)_3$, vanadium oxide, or mixtures of any two or more thereof, where Met is Al, Mg, Ti, B, Ga, Si, Mn, or Co; Met' is Mg, Zn, Al, Ga, B, Zr, or Ti; A is Li, Ag, Cu, Na, Mn, Fe, Co, Ni, Cu, and Zn; B is Ti, V, Cr, Fe, and Zr; X is P, S, Si, W, Mo; $0 \leq x \leq 0.3$, $0 \leq y \leq 0.5$, $0 \leq z \leq 0.5$, $0 \leq m \leq 0.5$ and $0 \leq n \leq 0.5$; $0 \leq x' \leq 0.4$, $0 \leq \alpha \leq 1$, $0 \leq \beta \leq 1$, $0 \leq \gamma \leq 1$, $0 \leq \delta \leq 0.4$, and $0 \leq z' \leq 0.4$; and $0 \leq n' \leq 3$. In some embodiments, the cathode includes a surface coating of a metal oxide on particles of the cathode. In some such embodiments, the metal oxide includes $ZrO_2$, $TiO_2$, $ZnO_2$, $WO_3$, $Al_2O_3$, MgO, $SiO_2$, $SnO_2$ $AlPO_4$, or $Al(OH)_3$. In some embodiments, the anode includes graphite, amorphous carbon, $Li_4Ti_5O_{12}$, tin alloys, silicon alloys, intermetallic compounds, or lithium metal.

In another aspect, an electrochemical device is provided including a spinel, olivine, or carbon-coated olivine cathode; a graphite or amorphous carbon anode; and a substantially non-aqueous electrolyte including an alkali metal salt that is $Li[BF_2(C_2O_4)]$ or $Li[B(C_2O_4)_2]$, a polar aprotic solvent that is ethyl acetate; propyl acetate; ethylene carbonate; propylene carbonate; dimethyl carbonate; diethyl carbonate; ethyl methyl carbonate; dimethyl ether; or γ-butyrolactone; a redox shuttle that is any of the compounds of Formulas I, II, or III as described above; and an electrode stabilizing compound that is pyridazine; vinyl pyridazine; quinoline; vinyl quinoline; pyridine; vinyl pyridine; indole; vinyl indole; triethanolamine; 1,3-dimethyl butadiene; butadiene; vinyl ethylene carbonate; vinyl carbonate; imidazole; vinyl imidazole; piperidine; vinyl piperidine; pyrimidine; vinyl pyrimidine; pyrazine; vinyl pyrazine; isoquinoline; vinyl isoquinoline; quinoxaline; vinyl quinoxaline; biphenyl; 1,2-diphenyl ether; 1,2-diphenylethane; o-terphenyl; N-methylpyrrole; naphthalene; 3,9-divinyl-2,4,8,10-tetraoxaspiro[5.5]undecane; 3,9-divinyl-2,4,8-trioxaspiro[5.5]undecane; 3,9-divinyl-2,4-dioxaspiro[5.5]undecane; 3,9-diethylidene-2,4,8,10-tetraoxaspiro[5.5]undecane; 3,9-diethylidene-2,4,8-trioxaspiro[5.5]undecane; 3,9-diethylidene-2,4-dioxaspiro[5.5]undecane; 3,9-dimethylene-2,4,8,10-tetraoxaspiro[5.5]undecane; 3,9-divinyl-1,5,7,11-tetraoxaspiro[5.5]undecane; 3,9-dimethylene-1,5,7,11-tetraoxaspiro[5.5]undecane; or 3,9-diethylidene-1,5,7,11-tetraoxaspiro[5.5]undecane.

In another aspect, a method of preparing an electrolyte includes combining an alkali metal salt; a polar aprotic solvent; and a compound of any of Formulas I, II, or III, as described above.

DETAILED DESCRIPTION

Figure 1:
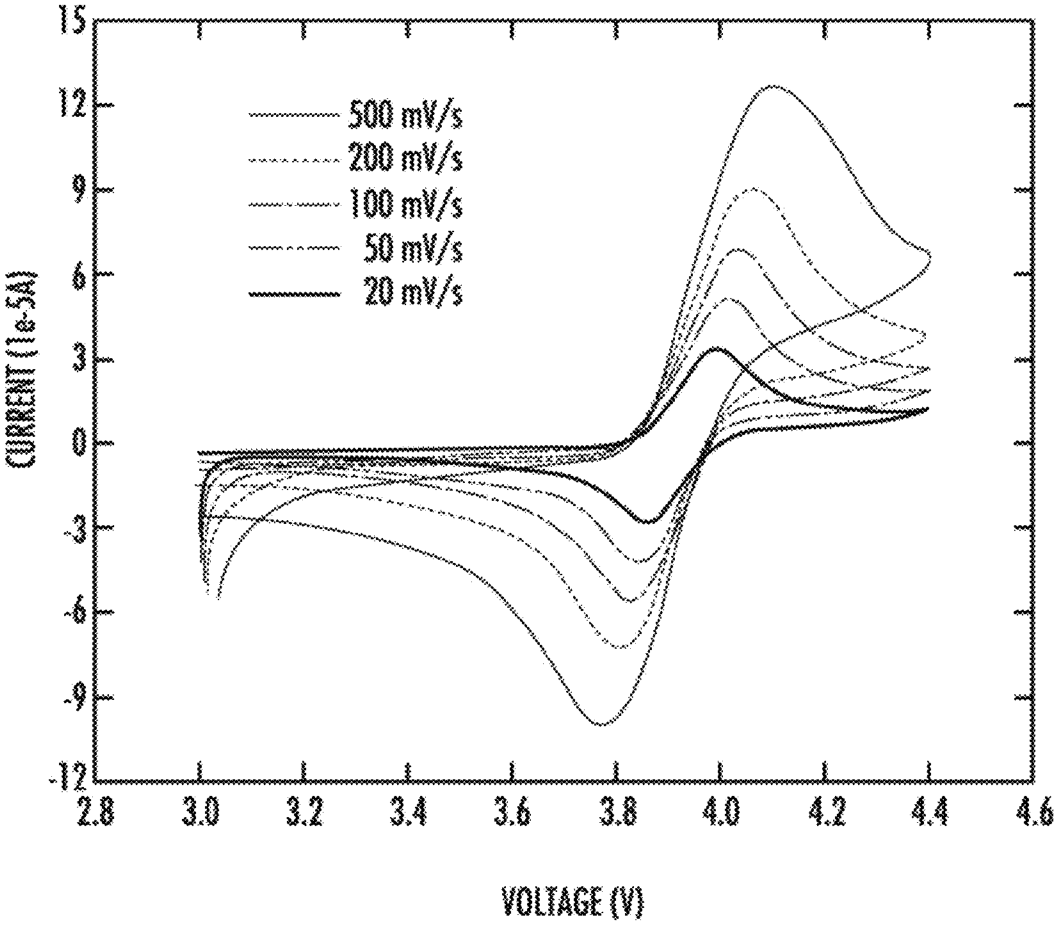
FIG. 1 is a series of cyclic voltammograms of 1,4-bis(2-methoxyethoxy)-2,5-di-tert-butyl-benzene (10 mM) in 1.2 M $LiPF_6$ in EC/EMC (3:7 by weight) using a three electrode system, at different scan rates.

In one aspect, compounds having at least one aromatic ring with two or more polyether or poly(ethylene oxide) (PEO) groups bonded through an oxygen to the aromatic ring are provided. Such compounds may be employed in a variety of applications. For example, in some embodiments, the compounds are redox shuttles that are capable of providing overcharge protection to an electrochemical cell and which exhibit sufficient solubility in carbonate-based electrolytes to allow for dissolution of the compounds sat acceptable levels.

According to one embodiment, the compound has Formula I, II, or III:

I

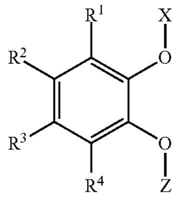

II

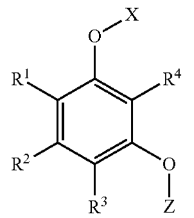

III

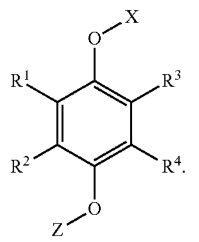

In such compounds, $R^1$, $R^2$, $R^3$, and $R^4$ are independently H, F, Cl, Br, CN, $NO_2$, a alkyl group, a haloalkyl group, a phosphate group, a polyether group; or $R^1$ and $R^2$, or $R^3$ and $R^4$, or in the case of Formula II $R^2$ and $R^3$ also may join together to form a fused ring on the benzene ring; and X and Z are independently a group of Formula A:

A

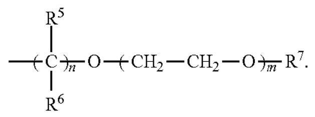

In the group of Formula A, $R^5$ and $R^6$ are independently H, F, Cl, Br, CN, $NO_2$, a alkyl group, a haloalkyl group, a phosphate group, or a polyether group; $R^7$ is H, a alkyl group, a haloalkyl group, a phosphate group, or a polyether group; n is an integer from 1 to 8; and m is an integer from 1 to 13. As used herein, the $CR^5R^6$ may be repeated n times, and in each individual unit, $R^5$ and $R^6$ are independently selected as indicated above. In some embodiments, $R^5$ and $R^6$ are H. In other embodiments, $R^5$ and $R^6$ at each occurrence are individually H, a $C_1$-$C_4$ alkyl, a $C_1$-$C_4$ haloalkyl, H, Cl, Br, or I. In yet other embodiments, $R^5$ and $R^6$ at each occurrence are individually H, methyl, ethyl, n-propyl, iso-propyl, n-butyl, sec-butyl, or tert-butyl. In some embodiments, $R^7$ is H or an alkyl group. In other embodiments, $R^7$ is H or a $C_1$-$C_4$ alkyl group. In some embodiments, $R^7$ is H, methyl, ethyl, n-propyl, iso-propyl, n-butyl, sec-butyl, or tert-butyl. In some embodiments, n is 1 to 3. In some embodiments, m is from 1 to 6.

In some embodiments, $R^1$, $R^2$, $R^3$, and $R^4$ are independently H, a alkyl group, a haloalkyl group, or a polyether group. In other embodiments, $R^1$, $R^2$, $R^3$, and $R^4$ are independently H, a $C_1$-$C_4$ alkyl group, a $C_1$-$C_4$ haloalkyl group, or a polyether group having from 2 to 20 carbon atoms. In some embodiments, $R^1$ and $R^4$ are the same and are different from that of $R^2$ and $R^3$. In some embodiments, $R^1$ and $R^4$ are individually an alkyl group or a haloalkyl group, and $R^2$ and $R^3$ are hydrogen. In some embodiments, $R^1$ and $R^4$ are individually methyl, ethyl, n-propyl, iso-propyl, n-butyl, sec-butyl, or tert-butyl and $R^2$ and $R^3$ are H. In one embodiment, for any of the compounds of Formula I, II, or III, at least one of $R^1$, $R^2$, $R^3$, and $R^4$ is other than H.

In some embodiments, $R^1$ and $R^4$ are the same and are different from that of $R^2$ and $R^3$. In some embodiments, $R^1$ and $R^4$ are individually an alkyl group or a haloalkyl group, and $R^2$ and $R^3$ are hydrogen. In some embodiments, $R^1$ and $R^4$ are individually methyl, ethyl, n-propyl, iso-propyl, n-butyl, sec-butyl, or tert-butyl and $R^2$ and $R^3$ are H.

In some embodiments, the compound is that of Formula I; $R^1$, $R^2$, $R^3$, and $R^4$ are independently H, a $C_1$-$C_4$ alkyl group, a $C_1$-$C_4$ haloalkyl group, or a polyether group having from 2 to 20 carbon atoms; $R^5$ and $R^6$ at each occurrence are individually H, a $C_1$-$C_4$ alkyl, a $C_1$-$C_4$ haloalkyl, H, Cl, Br, or I; $R^7$ is H or an alkyl group; n is 1 or 2; and m is from 1 to 8. In yet other embodiments, the compound is that of Formula I; $R^1$, $R^2$, $R^3$, and $R^4$ are independently H, methyl, ethyl, n-propyl, iso-propyl, n-butyl, sec-butyl, or tert-butyl, or a polyether group having from 2 to 20 carbon atoms; $R^5$ and $R^6$ at each occurrence are individually H or methyl; $R^7$ is H, methyl, ethyl, n-propyl, iso-propyl, n-butyl, sec-butyl, or tert-butyl; n is 1 or 2; and m is from 1 to 8. In some embodiments, the compound is that of Formula I; $R^1$ and $R^4$ are the same and are different from that of $R^2$ and $R^3$; $R^5$ and $R^6$ at each occurrence are individually H, a $C_1$-$C_4$ alkyl, a $C_1$-$C_4$ haloalkyl, H, Cl, Br, or I; $R^7$ is H or an alkyl group; n is 1 or 2; and m is from 1 to 8. In some embodiments, the compound is that of Formula I; $R^1$ and $R^4$ are individually an alkyl group or a haloalkyl group; $R^2$ and $R^3$ are hydrogen; $R^5$ and $R^6$ at each occurrence are individually H or methyl; $R^7$ is H, methyl, ethyl, n-propyl, iso-propyl, n-butyl, sec-butyl, or tert-butyl; n is 1 or 2; and m is from 1 to 8. In some embodiments, the compound is that of Formula I; $R^1$ and $R^4$ are tert-butyl; $R^2$ and $R^3$ are H; $R^5$ and $R^6$ at each occurrence are individually H or methyl; $R^7$ is H, methyl, or ethyl; n is 1 or 2; and m is 1 to 4.

In other embodiments, the compound is an aromatic compound substituted with at least one tertiary carbon organic group and at least one polyether group. Some compounds may contain two, or at least two, tertiary carbon organic groups which may be the same or different. If located on the same aromatic ring (e.g., a benzene ring), the tertiary carbon organic groups may be oriented ortho-, meta- or para- to one another. The polyether group may be a group of Formula A, as provided above. In some embodiments, the polyether groups have from 1 to 13 ethylene oxide ($—CH_2CH_2O—$) units. In other embodiments, the polyether groups have from 1 to 10 ethylene oxide units. In other embodiments, the polyether groups have from 2 to 6 ethylene oxide units. In other embodiments, the polyether groups have from 1 to 4 ethylene oxide units. In other embodiments, the polyether groups have from 1 to 3 ethylene oxide units. Some compounds may contain two or at least two polyether groups which may be the same or different. If located on the same aromatic ring the polyether groups may for example be oriented ortho-, meta- or para- to one another.

In some embodiments, as described above, $R^1$ and $R^2$, or $R^3$ and $R^4$, or in the case of Formula II $R^2$ and $R^3$ may join together to form a fused ring on the benzene ring. The compound may include from 1 to 3 aromatic rings that are fused or connected to the benzene ring. Each aromatic ring may for example be carbocyclic. Examples of such aromatic rings include benzene, naphthalene, anthracene, biphenyl, and the like.

Such compounds include substituted di-oligo(ethylene glycol)benzenes, such as, 2-methyl-1,4-di-oligo(ethylene glycol)benzene, 2,3-dimethyl-1,4-di-oligo(ethylene glycol) benzene, 2,5-dimethyl-1,4-di-oligo(ethylene glycol)benzene, 2,6-dimethyl-1,4-di-oligo(ethylene glycol)benzene, 2,3,6-trimethyl-1,2-di-oligo(ethylene glycol)benzene, 2,3,5,6-tetramethyl-1,4-di-oligo(ethylene glycol)benzene, 4-methyl-1,2-di-oligo(ethylene glycol)benzene, 2,3,5,6-tetramethyl-1,4-di-oligo(ethylene glycol)benzene, 2-ethyl-1,4-di-oligo(ethylene glycol)benzene, 2,3-diethyl-1,4-di-oligo (ethylene glycol)benzene, 2,5-diethyl-1,4-di-oligo(ethylene glycol)benzene, 2,6-diethyl-1,4-di-oligo(ethylene glycol) benzene, 2,3,6-triethyl-1,2-di-oligo(ethylene glycol)benzene, 2,3,5,6-tetraethyl-1,4-di-oligo(ethylene glycol)benzene, 4-ethyl-1,2-di-oligo(ethylene glycol)benzene, 2,5-diisopropyl-1,4-di-oligo(ethylene glycol)benzene, 2-tert-butyl-1,4-di-oligo(ethylene glycol)benzene, 2,3-di-tert-butyl-1,4-di-oligo(ethylene glycol)benzene, 2,5-di-tert-butyl-1,4-di-oligo(ethylene glycol)benzene, 2,5-di-tert-pentyl-1,4-di-oligo(ethylene glycol)benzene, 2,5-di-tert-butyl-3,6-di-nitro-1,4-di-oligo(ethylene glycol)benzene, 2,5-di-tert-butyl-3,6-di-cyano-1,4-di-oligo(ethylene glycol) benzene, 2,5-di-tert-butyl-1,4-di-oligo(ethylene glycol) benzene, 2,5-dicyclohexyl-1,4-di-oligo(ethylene glycol) benzene, 4-tert-butyl-1,2-di-oligo(ethylene glycol)benzene, 4,5-di-tert-butyl-1,2-di-oligo(ethylene glycol)benzene, 4,5-di-tert-pentyl-1,2-di-oligo(ethylene glycol)benzene and 4,5-di-tert-butyl-1,2-diethoxybenzene; substituted oligo(ethylene glycol)naphthalenes, such as, 4,8-di-tert-butyl-1,5-di-oligo(ethylene glycol)naphthalene; polycyclic compounds, such as, 9,10-di-oligo(ethylene glycol)-1,4:5,8-dimethano-1,2,3,4,5,6,7,8-octahydroanthracene and 9,10-di-oligo(ethylene glycol)-1,4:5,8-diethano-1,2,3,4,5,6,7,8-octahydroanthracene.

According to some embodiments, the compound is 1,4-bis (2-methoxy)ethoxy-2,5-di-tert-butyl-benzene; 1,4-bis(2-(2-methoxy)ethoxy)ethoxy-2,5-di-tert-butyl-benzene; 1,4-bis (2-(2-(2-methoxy)ethoxy)ethoxy)ethoxy-2,5-di-tert-butyl-benzene; or 1,4-bis(2-(2-(2-(2-methoxy)ethoxy)ethoxy) ethoxy)ethoxy-2,5-di-tert-butyl-benzene.

In another aspect, the above compounds are employed as redox shuttles in an electrolyte. According to one embodiment, the redox shuttle is a compound of Formula I, II, or III, as described above. In other embodiments, the redox shuttle is a compound of Formula I, as described above. Such compounds have been determined to have good compatibility with carbonate-based electrolytes. Such electrolytes, employing the compounds as redox shuttles, provide overcharge protection to lithium-ion batteries.

According to one embodiment, the redox shuttle has Formula I, II, or III:

I

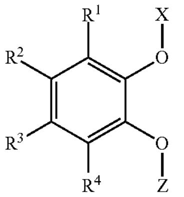

-continued

II

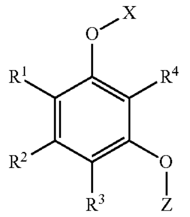

III

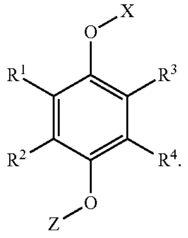

In such redox shuttles, $R^1$, $R^2$, $R^3$, and $R^4$ are independently H, F, Cl, Br, CN, $NO_2$, a alkyl group, a haloalkyl group, a phosphate group, a polyether group; or $R^1$ and $R^2$, or $R^3$ and $R^4$, or in the case of Formula II $R^2$ and $R^3$ also may join together to form a fused ring on the benzene ring; and X and Z are independently a group of Formula A:

A

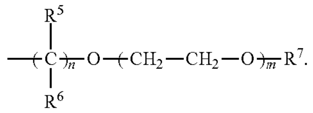

In the group of Formula A, $R^5$ and $R^6$ are independently H, F, Cl, Br, CN, $NO_2$, a alkyl group, a haloalkyl group, a phosphate group, or a polyether group; $R^7$ is H, a alkyl group, a haloalkyl group, a phosphate group, or a polyether group; n is an integer from 1 to 8; and m is an integer from 1 to 13. As used herein, the $CR^5R^6$ may be repeated n times, and in each individual unit, $R^5$ and $R^6$ are independently selected as indicated above. In some embodiments, $R^5$ and $R^6$ are H. In other embodiments, $R^5$ and $R^6$ at each occurrence are individually H, a $C_1$-$C_4$ alkyl, a $C_1$-$C_4$ haloalkyl, H, Cl, Br, or I. In yet other embodiments, $R^5$ and $R^6$ at each occurrence are individually H, methyl, ethyl, n-propyl, iso-propyl, n-butyl, sec-butyl, or tert-butyl. In some embodiments, $R^7$ is H or an alkyl group. In other embodiments, $R^7$ is H or a $C_1$-$C_4$ alkyl group. In some embodiments, $R^7$ is H, methyl, ethyl, n-propyl, iso-propyl, n-butyl, sec-butyl, or tert-butyl. In some embodiments, n is 1 to 2. In some embodiments, m is from 1 to 4.

In some embodiments, $R^1$, $R^2$, $R^3$, and $R^4$ are independently H, a alkyl group, a haloalkyl group, or a polyether group. In other embodiments, $R^1$, $R^2$, $R^3$, and $R^4$ are independently H, a $C_1$-$C_4$ alkyl group, a $C_1$-$C_4$ haloalkyl group, or a polyether group having from 2 to 20 carbon atoms. In some embodiments, $R^1$ and $R^4$ are the same and are different from that of $R^2$ and $R^3$. In some embodiments, $R^1$ and $R^4$ are individually an alkyl group or a haloalkyl group, and $R^2$ and $R^3$ are hydrogen. In some embodiments, $R^1$ and $R^4$ are individually methyl, ethyl, n-propyl, iso-propyl, n-butyl, sec-butyl, or tert-butyl and $R^2$ and $R^3$ are H.

In some embodiments, $R^1$ and $R^4$ are the same and are different from that of $R^2$ and $R^3$. In some embodiments, $R^1$ and $R^4$ are individually an alkyl group or a haloalkyl group, and $R^2$ and $R^3$ are hydrogen. In some embodiments, $R^1$ and $R^4$ are individually methyl, ethyl, n-propyl, iso-propyl, n-butyl, sec-butyl, or tert-butyl and $R^2$ and $R^3$ are H.

In some embodiments, the redox shuttle is that of Formula I; $R^1$, $R^2$, $R^3$, and $R^4$ are independently H, a $C_1$-$C_4$ alkyl group, a $C_1$-$C_4$ haloalkyl group, or a polyether group having from 2 to 20 carbon atoms; $R^5$ and $R^6$ at each occurrence are individually H, a $C_1$-$C_4$ alkyl, a $C_1$-$C_4$ haloalkyl, H, Cl, Br, or I; $R^7$ is H or an alkyl group; n is 1 or 2; and m is from 1 to 8. In yet other embodiments, the redox shuttle is that of Formula I; $R^1$, $R^2$, $R^3$, and $R^4$ are independently H, methyl, ethyl, n-propyl, iso-propyl, n-butyl, sec-butyl, or tert-butyl, or a polyether group having from 2 to 20 carbon atoms; $R^5$ and $R^6$ at each occurrence are individually H or methyl; $R^7$ is H, methyl, ethyl, n-propyl, iso-propyl, n-butyl, sec-butyl, or tert-butyl; n is 1 or 2; and m is from 1 to 8. In some embodiments, the redox shuttle is that of Formula I; $R^1$ and $R^4$ are the same and are different from that of $R^2$ and $R^3$; $R^5$ and $R^6$ at each occurrence are individually H, a $C_1$-$C_4$ alkyl, a $C_1$-$C_4$ haloalkyl, H, Cl, Br, or I; $R^7$ is H or an alkyl group; n is 1 or 2; and m is from 1 to 8. In some embodiments, the redox shuttle is that of Formula I; $R^1$ and $R^4$ are individually an alkyl group or a haloalkyl group; $R^2$ and $R^3$ are hydrogen; $R^5$ and $R^6$ at each occurrence are individually H or methyl; $R^7$ is H, methyl, ethyl, n-propyl, iso-propyl, n-butyl, sec-butyl, or tert-butyl; n is 1 or 2; and m is from 1 to 8. In some embodiments, the redox shuttle is that of Formula I; $R^1$ and $R^4$ are tert-butyl; $R^2$ and $R^3$ are H; $R^5$ and $R^6$ at each occurrence are individually H or methyl; $R^7$ is H, methyl, or ethyl; n is 1 or 2; and m is 1 to 4.

In other embodiments, the redox shuttle is an aromatic redox shuttle substituted with at least one tertiary carbon organic group and at least one polyether group. Some redox shuttles may contain two, or at least two, tertiary carbon organic groups which may be the same or different. If located on the same aromatic ring (e.g., a benzene ring), the tertiary carbon organic groups may be oriented ortho-, meta- or para- to one another. The polyether group may be a group of Formula A, as provided above. In some embodiments, the polyether groups have from 1 to 13 ethylene oxide (—$CH_2CH_2O$—) units. In other embodiments, the polyether groups have from 1 to 10 ethylene oxide units. In other embodiments, the polyether groups have from 2 to 6 ethylene oxide units. In other embodiments, the polyether groups have from 1 to 4 ethylene oxide units. In other embodiments, the polyether groups have from 1 to 3 ethylene oxide units. Some compounds may contain two or at least two polyether groups which may be the same or different. If located on the same aromatic ring the polyether groups may for example be oriented ortho-, meta- or para- to one another.

In some embodiments, as described above, $R^1$ and $R^2$, or $R^3$ and $R^4$, or in the case of Formula II $R^2$ and $R^3$ may join together to form a fused ring on the benzene ring. The redox shuttle may include from 1 to 3 aromatic rings that are fused or connected to the benzene ring. Each aromatic ring may for example be carbocyclic. Examples of such aromatic rings include benzene, naphthalene, anthracene, biphenyl, and the like. Other substituents may be present on the shuttle aromatic ring or rings or on the tertiary carbon organic group(s) or alkoxy group(s), so long as such substituents do not unduly interfere with factors such as the shuttle's charge-carrying capability, oxidation potential or stability.

Such redox shuttles include, substituted di-oligo(ethylene glycol)benzenes, such as, 2-methyl-1,4-di-oligo(ethylene glycol)benzene, 2,3-dimethyl-1,4-di-oligo(ethylene glycol) benzene, 2,5-dimethyl-1,4-di-oligo(ethylene glycol)benzene, 2,6-dimethyl-1,4-di-oligo(ethylene glycol)benzene, 2,3,6-trimethyl-1,2-di-oligo(ethylene glycol)benzene, 2,3,5,6-tetramethyl-1,4-di-oligo(ethylene glycol)benzene, 4-methyl-1,2-di-oligo(ethylene glycol)benzene, 2,3,5,6-tetramethyl-1,4-di-oligo(ethylene glycol)benzene, 2-ethyl-1,4-di-oligo(ethylene glycol)benzene, 2,3-diethyl-1,4-di-oligo (ethylene glycol)benzene, 2,5-diethyl-1,4-di-oligo(ethylene glycol)benzene, 2,6-diethyl-1,4-di-oligo(ethylene glycol) benzene, 2,3,6-triethyl-1,2-di-oligo(ethylene glycol)benzene, 2,3,5,6-tetraethyl-1,4-di-oligo(ethylene glycol)benzene, 4-ethyl-1,2-di-oligo(ethylene glycol)benzene, 2,5-diisopropyl-1,4-di-oligo(ethylene glycol)benzene, 2-tert-butyl-1,4-di-oligo(ethylene glycol)benzene, 2,3-di-tert-butyl-1,4-di-oligo(ethylene glycol)benzene, 2,5-di-tert-butyl-1,4-di-oligo(ethylene glycol)benzene, 2,5-di-tert-pentyl-1,4-di-oligo(ethylene glycol)benzene, 2,5-di-tert-butyl-3,6-di-nitro-1,4-di-oligo(ethylene glycol)benzene, 2,5-di-tert-butyl-3,6-di-cyano-1,4-di-oligo(ethylene glycol) benzene, 2,5-di-tert-butyl-1,4-di-oligo(ethylene glycol) benzene, 2,5-dicyclohexyl-1,4-di-oligo(ethylene glycol) benzene, 4-tert-butyl-1,2-di-oligo(ethylene glycol)benzene, 4,5-di-tert-butyl-1,2-di-oligo(ethylene glycol)benzene, 4,5-di-tert-pentyl-1,2-di-oligo(ethylene glycol)benzene and 4,5-di-tert-butyl-1,2-diethoxybenzene; substituted oligo(ethylene glycol)naphthalenes, such as, 4,8-di-tert-butyl-1,5-di-oligo(ethylene glycol)naphthalene; polycyclic compounds, such as, 9,10-di-oligo(ethylene glycol)-1,4:5,8-dimethano-1,2,3,4,5,6,7,8-octahydroanthracene and 9,10-di-oligo(ethylene glycol)-1,4:5,8-diethano-1,2,3,4,5,6,7,8-octahydroanthracene.

According to some embodiments, the redox shuttle is 1,4-bis(2-methoxy)ethoxy-2,5-di-tert-butyl-benzene; 1,4-bis(2-(2-methoxy)ethoxy)ethoxy-2,5-di-tert-butyl-benzene; 1,4-bis(2-(2-(2-methoxy)ethoxy)ethoxy)ethoxy-2,5-di-tert-butyl-benzene; or 1,4-bis(2-(2-(2-(2-methoxy)ethoxy)ethoxy)ethoxy)ethoxy-2,5-di-tert-butyl-benzene.

The redox shuttles operate in an electrochemical range defined by the characteristics of the positive electrode and which can provide over-discharge protection in series-connected cells. A negative electrode having a larger irreversible first cycle capacity loss than that of the positive electrode is employed, so that if a cell is driven into reversal. the potential of the negative electrode is driven above that of the positive electrode. During over-discharge, the potential of the negative electrode therefore increases. However, the shuttle limits the negative electrode potential to a value slightly above that of the positive electrode maximum normal operating potential and prevents the negative electrode from reaching even higher and more destructive potentials. A negative electrode current collector whose lithium alloying potential is below the negative electrode minimum normal operating potential is also employed. This prevents the current collector from capturing lithium during recharging of the Li-ion cell. The resulting battery chemically limits or eliminates cell damage due to repeated over-discharge even though the negative electrode in a weak cell may be driven to a value more positive than the positive electrode potential.

A variety of redox shuttles may be employed in lithium-ion batteries. Suitable redox shuttles have an electrochemical potential above (e.g., slightly above) the positive electrode's maximum normal operating potential. Thus, according to some embodiments, redox shuttles in the electrolytes, have a redox potential from 3.5 V to 5.0 V. In other embodiments, the redox shuttles have a redox potential from 3.6 V to 4.6 V.

The redox shuttle selection may be guided in part by the positive electrode selection. As a general numeric guide, the shuttle may have a redox potential from 0.3 V to 0.6 V above the positive electrode's maximum normal operating potential, e.g., from 3.7 to 4.7 V vs. $Li/Li^+$, from 3.7 V to 4.4 V vs. $Li/Li^+$, from 3.7 V to 4.2 V vs. $Li/Li^+$, or from 3.7 V to 4.0 V vs. $Li/Li^+$ above the positive electrode's maximum normal operating potential. For example, $LiFePO_4$ positive electrodes have a recharge plateau of around 3.45 V vs. $Li/Li^+$, and redox shuttles for use with such electrodes may have a redox potential from 3.75 V to about 4.05 V vs. $Li/Li^+$. Similarly, $LiMnPO_4$ and $LiMn_2O_4$ electrodes have a recharge plateau around 4.1V vs. $Li/Li^+$, and redox shuttles for use with such electrodes may have a redox potential from 4.4 V to 4.7 V vs. $Li/Li^+$.

Mixtures of two or more shuttles having different electrochemical potentials vs. $Li/Li^+$ may also be employed. For example, a first shuttle operative at 3.8V and a second shuttle operative at 3.9V may both be employed in a single cell. If after many charge/discharge cycles the first shuttle degrades and loses its effectiveness, the second shuttle (which would not meanwhile have been oxidized to form its radical cation while the first shuttle was operative) could take over and provide a further (albeit higher potential) margin of safety against overcharge or over-discharge damage.

According to some embodiments, in addition to the redox shuttle, the electrolyte includes a polar aprotic solvent, and a lithium metal salt. The electrolytes are substantially non-aqueous. As used herein, substantially non-aqueous means that the electrolytes do not contain water, or if water is present, it is only present at trace levels. For example, where the water is present at trace levels it is present at less than 20 ppm.

A variety of solvents may be employed in the electrolyte as the polar aprotic solvent. Suitable polar aprotic solvents include liquids and gels capable of solubilizing sufficient quantities of the lithium salt and the redox shuttle so that a suitable quantity of charge can be transported from the positive electrode to negative electrode. The solvents can be used over a wide temperature range, e.g., from −30° C. to 70° C. without freezing or boiling, and are stable in the electrochemical range within which the cell electrodes and shuttle operate. Suitable solvents include dimethyl carbonate; ethyl methyl carbonate; diethyl carbonate; methyl propyl carbonate; ethyl propyl carbonate; dipropyl carbonate; bis(trifluoroethyl) carbonate; bis(pentafluoropropyl) carbonate; trifluoroethyl methyl carbonate; pentafluoroethyl methyl carbonate; heptafluoropropyl methyl carbonate; perfluorobutyl methyl carbonate; trifluoroethyl ethyl carbonate; pentafluoroethyl ethyl carbonate; heptafluoropropyl ethyl carbonate; perfluorobutyl ethyl carbonate; fluorinated oligomers; dimethoxyethane; triglyme; dimethylvinylene carbonate; tetraethyleneglycol; dimethyl ether; polyethylene glycols; sulfones; and γ-butyrolactone.

The redox shuttles, as noted above, have suitable solubility in carbonate-based electrolyte solvents and gels. For example, the redox shuttles may be prepared in carbonate-based electrolytes, such as, 1.2M $LiPF_6$ in EC/EMC 3/7 (i.e. an mixture of 3 parts ethylene carbonate and 7 parts ethylmethylcarbonate), or 1.2M $LiPF_6$ in EC/DEC 5/5 (i.e. a 1:1 mixture of ethylene carbonate and diethylcarbonate). According to various embodiments, electrolytes may be prepared with a redox shuttle at a concentration of from 0.005 wt % to 50 wt %, or from 0.1 wt % to 30 wt %. In other embodiments, the electrolytes may be prepared with a redox shuttle at a concentration of from 2% to 10%.

Suitable lithium salts that may be used in the electrolytes, include, but are not limited to, $Li[B(C_2O_4)_2]$; $Li[BF_2(C_2O_4)]$; $LiClO_4$; $LiBF_4$; $LiAsF_6$; $LiSbF_6$; LiBr, $LiPF_6$; $Li[CF_3SO_3]$; $Li[N(CF_3SO_2)_2]$; $Li[C(CF_3SO_2)_3]$; $Li[B(C_6F_5)_4]$; $Li[B(C_6H_5)_4]$; $Li[N(SO_2CF_3)_2]$; $Li[N(SO_2CF_2CF_3)_2]$; $LiN(SO_2C_2F_5)_2$; $Li[BF_3C_2F_5]$; and $Li[PF_3(CF_2CF_3)_3]$; and lithium alkyl fluorophosphates.

In some aspects, the electrolytes may include other additives to enhance the performance of the electrolyte when used in an electrochemical cell. For example, the electrolytes may also include an electrode stabilizing compound to protect the electrodes from degradation. Such electrode stabilizing compounds are described by co-pending U.S. patent application Ser. Nos. 10/857,365 and 11/279,120. Such electrode stabilizing compounds can be reduced or polymerized on the surface of a negative electrode to form a passivation film on the surface of the negative electrode. Likewise, electrolytes can include an electrode stabilizing compound that can be oxidized or polymerized on the surface of the positive electrode to form a passivation film on the surface of the positive electrode. In some embodiments, the electrolytes further include mixtures of the two types of electrode stabilizing compounds. The compounds are typically present at a concentration of from 0.001 wt % to 8 wt %.

In some embodiments, the electrode stabilizing compound is a substituted or unsubstituted linear, branched or cyclic hydrocarbon including at least one oxygen atom and at least one aryl, alkenyl or alkynyl group. Passivating films may be formed from a substituted aryl compound or a substituted or unsubstituted heteroaryl compound where the compound includes at least one oxygen atom. Alternatively, a combination of two compounds may be used. In some embodiments, one compound is selective for forming a passivating film on the cathode to prevent leaching of metal ions and the other compound can be selective for passivating the anode surface to prevent or lessen the reduction of metal ions at the anode. Representative electrode stabilizing compounds include 1,2-divinyl furoate, 1,3-butadiene carbonate, 1-vinylazetidin-2-one, 1-vinylaziridin-2-one, 1-vinylpiperidin-2-one, 1 vinylpyrrolidin-2-one, 2,4-divinyl-1,3-dioxane, 2 amino-3 vinylcyclohexanone, 2-amino-3-vinylcyclopropanone, 2 amino-4-vinylcyclobutanone, 2-amino-5-vinylcyclopentanone, 2-aryloxy-cyclopropanone, 2-vinyl-[1,2]oxazetidine, 2 vinylaminocyclohexanol, 2-vinylaminocyclopropanone, 2 vinyloxetane, 2-vinyloxy-cyclopropanone, 3-(N-vinylamino)cyclohexanone, 3,5-divinyl furoate, 3-vinylazetidin-2-one, 3 vinylaziridin 2 one, 3 vinylcyclobutanone, 3 vinylcyclopentanone, 3 vinyloxaziridine, 3 vinyloxetane, 3-vinylpyrrolidin-2-one, 4,4 divinyl-3 dioxolan 2-one, 4 vinyltetrahydropyran, 5-vinylpiperidin-3-one, allylglycidyl ether, butadiene monoxide, butyl vinyl ether, dihydropyran-3-one, divinyl butyl carbonate, divinyl carbonate, divinyl crotonate, divinyl ether, divinyl ethylene carbonate, divinyl ethylene silicate, divinyl ethylene sulfate, divinyl ethylene sulfite, divinyl methoxypyrazine, divinyl methylphosphate, divinyl propylene carbonate, ethyl phosphate, methoxy-o-terphenyl, methyl phosphate, oxetan-2-yl-vinylamine, oxiranylvinylamine, vinyl carbonate, vinyl crotonate, vinyl cyclopentanone, vinyl ethyl-2-furoate, vinyl ethylene carbonate, vinyl ethylene silicate, vinyl ethylene sulfate, vinyl ethylene sulfite, vinyl methacrylate, vinyl phosphate, vinyl-2-furoate, vinylcylopropanone, vinylethylene oxide, β-vinyl-γ-butyrolactone, or a mixture of any two or more thereof. In some embodiments the electrode stabilizing compound may be a cyclotriphosphazene that is substituted with F, alkyloxy, alkenyloxy, aryloxy, methoxy, allyloxy groups, or combinations thereof. For example, the compound may be a (divinyl)-(methoxy)(trifluoro)cyclotriphosphazene, (trivinyl)(difluoro)(methoxy)cyclotriphosphazene, (vinyl)(methoxy)(tetrafluoro)cyclotriphosphazene, (aryloxy)(tetrafluoro)(methoxy)-cyclotriphosphazene, (diaryloxy)(trifluoro)(methoxy)cyclotriphosphazene compounds, or a mixture of two or more such compounds. In some embodiments, the electrode stabilizing compound is vinyl ethylene carbonate, vinyl carbonate, or 1,2-diphenyl ether, or a mixture of any two or more such compounds.

Other representative electrode stabilizing compounds may include compounds with phenyl, naphthyl, anthracenyl, pyrrolyl, oxazolyl, furanyl, indolyl, carbazolyl, imidazolyl, or thiophenyl groups. For example, electrode stabilizing compounds may be aryloxpyrrole, aryloxy ethylene sulfate, aryloxy pyrazine, aryloxy-carbazole trivinylphosphate, aryloxy-ethyl-2-furoate, aryloxy-o-terphenyl, aryloxy-pyridazine, butyl-aryloxy-ether, divinyl diphenyl ether, (tetrahydro-furan-2-yl)-vinylamine, divinyl methoxybipyridine, methoxy-4-vinylbiphenyl, vinyl methoxy carbazole, vinyl methoxy piperidine, vinyl methoxypyrazine, vinyl methyl carbonate-allylanisole, vinyl pyridazine, 1-divinylimidazole, 3-vinyltetrahydrofuran, divinyl furan, divinyl methoxy furan, divinylpyrazine, vinyl methoxy imidazole, vinylmethoxy pyrrole, vinyl-tetrahydrofuran, 2,4-divinyl isooxazole, 3,4 divinyl-1-methylpyrrole, aryloxyoxetane, aryloxy-phenyl carbonate, aryloxy-piperidine, aryloxy-tetrahydrofuran, 2-aryl-cyclopropanone, 2-diaryloxy-furoate, 4-allylanisole, aryloxy-carbazole, aryloxy-2-furoate, aryloxy-crotonate, aryloxy-cyclobutane, aryloxy-cyclopentanone, aryloxy-cyclopropanone, aryloxy-cyclolophosphazene, aryloxy-ethylene silicate, aryloxy-ethylene sulfate, aryloxy-ethylene sulfite, aryloxy-imidazole, aryloxy-methacrylate, aryloxy-phosphate, aryloxy-pyrrole, aryloxyquinoline, diaryloxycyclotriphosphazene, diaryloxy ethylene carbonate, diaryloxy furan, diaryloxy methyl phosphate, diaryloxy-butyl carbonate, diaryloxy-crotonate, diaryloxy-diphenyl ether, diaryloxy-ethyl silicate, diaryloxy-ethylene silicate, diaryloxy-ethylene sulfate, diaryloxyethylene sulfite, diaryloxy-phenyl carbonate, diaryloxy-propylene carbonate, diphenyl carbonate, diphenyl diaryloxy silicate, diphenyl divinyl silicate, diphenyl ether, diphenyl silicate, divinyl methoxydiphenyl ether, divinyl phenyl carbonate, methoxycarbazole, or 2,4-dimethyl-6-hydroxy-pyrimidine, vinyl methoxyquinoline, pyridazine, vinyl pyridazine, quinoline, vinyl quinoline, pyridine, vinyl pyridine, indole, vinyl indole, triethanolamine, 1,3-dimethyl butadiene, butadiene, vinyl ethylene carbonate, vinyl carbonate, imidazole, vinyl imidazole, piperidine, vinyl piperidine, pyrimidine, vinyl pyrimidine, pyrazine, vinyl pyrazine, isoquinoline, vinyl isoquinoline, quinoxaline, vinyl quinoxaline, biphenyl, 1,2-diphenyl ether, 1,2-diphenylethane, o terphenyl, N-methylpyrrole, naphthalene, or a mixture of any two or more such compounds.

In other embodiments, electrode stabilizing compounds include substituted or unsubstituted spirocyclic hydrocarbons containing at least one oxygen atom and at least one alkenyl or alkynyl group. For example, such stabilizing compounds include those having Formula V:

(V)

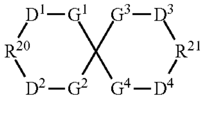

where: $D^1$, $D^2$, $D^3$, and $D^4$ are independently O or $CR^{22}R^{23}$; provided that $D^1$ is not O when $G^1$ is O, $D^2$ is not O when $G^2$ is O, $D^3$ is not O when $G^3$ is O, and $D^4$ is not O when $G^4$ is O; $G^1$, $G^2$, $G^3$, and $G^4$ are independently O or $CR^{22}R^{23}$; provided that $G^1$ is not O when $D^1$ is O, $G^2$ is not O when $D^2$ is O, $G^3$ is not O when $D^3$ is O, and $G^4$ is not O when $D^4$ is O; $R^{20}$ and $R^{21}$ are independently a substituted or unsubstituted divalent alkenyl or alkynyl group; $R^{22}$ and $R^{23}$ at each occurrence are independently H, F, Cl, a substituted or an unsubstituted alkyl, alkenyl, or alkynyl group.

Representative examples of Formula V include, but are not limited to, 3,9 divinyl-2,4,8,10-tetraoxaspiro[5.5]undecane, 3,9-divinyl-2,4,8-trioxaspiro[5.5]undecane, 3,9-divinyl-2,4-dioxaspiro[5.5]undecane, 3,9-diethylidene-2,4,8,10-tetraoxaspiro[5.5]undecane, 3,9-diethylidene-2,4,8-trioxaspiro[5.5]undecane, 3,9-diethylidene-2,4-dioxaspiro[5.5]undecane, 3,9-dimethylene-2,4,8,10-tetraoxaspiro[5.5]undecane, 3,9-divinyl-1,5,7,11-tetraoxaspiro[5.5]undecane, 3,9 dimethylene-1,5,7,11-tetraoxaspiro[5.5]undecane, 3,9-diethylidene-1,5,7,11-tetraoxaspiro[5.5]undecane, or a mixture of any two or more such compounds. Furthermore, mixtures of any two or more electrode stabilizing compounds may also be used in the electrolytes.

In some embodiments, the electrode stabilizing compound is an anion receptor. In some embodiments, the anion receptor is a Lewis acid. In other embodiments, the anion receptor is a borane, a boronate, a borate, a borole, or a mixture of any two or more such compounds. In some embodiments, the anion receptor is a compound of the Formula VI:

VI

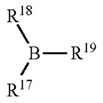

where, each $R^{17}$, $R^{18}$, and $R^{19}$ are independently halogen, alkyl, aryl, halogen-substituted alkyl, halogen-substituted aryl, or $OR^{17}$; or any two of $R^{17}$, $R^{18}$, and $R^{19}$, together with the atoms to which they are attached, form a heterocyclic ring having 5-9 members, and $R^{17}$ is at each occurrence independently alkyl, aryl, halogen-substituted alkyl, or halogen-substituted aryl.

In some embodiments, the anion receptors include, but not limited to, tri(propyl)borate, tris(1,1,1,3,3,3-hexafluoro-propan-2-yl)borate, tris(1,1,1,3,3,3-hexafluoro-2-phenyl-propan-2-yl)borate, tris(1,1,1,3,3,3-hexafluoro-2-(trifluoromethyl)propan-2-yl)borate, triphenyl borate, tris(4-fluorophenyl)borate, tris(2,4-difluorophenyl)borate, tris(2,3,5,6-tetrafluorophenyl)borate, tris(pentafluorophenyl)borate, tris(3-(trifluoromethyl)phenyl)borate, tris(3,5-bis(trifluoromethyl)phenyl)borate, tris(pentafluorophenyl)borane, or a mixture of any two or more thereof. Further suitable compounds include 2-(2,4-difluorophenyl)-4-fluoro-1,3,2-benzodioxaborole, 2-(3-trifluoromethyl phenyl)-4-fluoro-1,3,2-benzodioxaborole, 2,5-bis(trifluoromethyl)phenyl-4-fluoro-1,3,2-benzodioxaborole, 2-(4-fluorophenyl)-tetrafluoro-1,3,2-benzodioxaborole, 2-(2,4-difluorophenyl)-tetrafluoro-1,3,2-benzodioxaborole, 2-(pentafluorophenyl)-tetrafluoro-1,3,2-benzodioxaborole, 2-(2-trifluoromethyl phenyl)-tetrafluoro-1,3,2-benzodioxaborole, 2,5-bis(trifluoromethyl phenyl)-tetrafluoro-1,3,2-benzodioxaborole, 2-phenyl-4,4,5,5-tetra(trifluoromethyl)-1,3,2-benzodioxaborolane, 2-(3,5-difluorophenyl-4,4,5,5-tetrakis(trifluoromethyl)-1,3,2-dioxaborolane, 2-(3,5-difluorophenyl-4,4,5,5-tetrakis(trifluoromethyl)-1,3,2-dioxaborolane, 2-pentafluorophenyl-4,4,5,5-tetrakis(trifluoromethyl)-1,3,2-dioxaborolane, bis(1,1,1,3,3,3-hexafluoroisopropyl)phenyl-boronate, bis(1,1,1,3,3,3-hexafluoroisopropyl)-3,5-difluorophenylboronate, bis(1,1,1,3,3,3-hexafluoroisopropyl)pentafluorophenylboronate, or a mixture of any two or more such compounds. In some embodiments, each anion receptor is present at a concentration from 0.001 wt % to 10 wt %.

In some other embodiments, the electrolyte includes as an electrolyte compound, $Li_2B_{12}X_{12-n}H_n$, $Li_2B_{10}X_{10-n'}H_{n'}$, or a mixture of two or more of such compounds. Such electrolyte compounds may be present from 0.001 wt % to 15 wt %. In such compounds, X is OH, $OCH_3$, F, Cl, Br, or I, n is an integer from 0 to 12, and n' is an integer from 0 to 10.

In some embodiments, the electrolyte further includes a gel. Such electrolytes include a polar aprotic solvent; a lithium salt; a redox shuttle; a crosslinking agent; monofunctional monomeric compound; and at least one radical reaction initiator. In some embodiments, the gel electrolyte can also include other electrode stabilization compounds and other electrolyte compounds. Suitable crosslinking agents may be represented by Formula VII:

VII

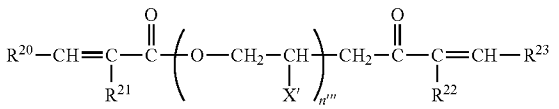

where $R^{20}$, $R^{21}$, $R^{22}$, and $R^{23}$ are each independently hydrogen, a substituted or unsubstituted alkyl group having from 1 to 12 carbon atoms, or a substituted or unsubstituted alkenyl group having from 2 to 12 carbon atoms; and where X' is a hydrogen, methyl, or ethyl group, and n''' is an integer from 1 to 15. Monofunctional monomeric compounds may be used for the control of the crosslinking density of the gel electrolyte. Suitable monofunctional monomeric compounds include those of Formula VIII:

VIII

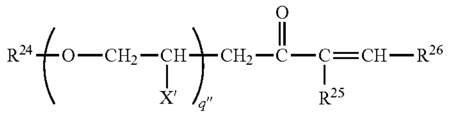

where $R^{24}$ is an alkyl group having from 1 to 12 carbon atoms; $R^{25}$ and $R^{26}$ are each independently a hydrogen, a substituted or unsubstituted alkyl group having from 1 to 12 carbon atoms, or a substituted or unsubstituted alkenyl group having from 2 to 12 carbon atoms; X' is hydrogen, methyl or ethyl group; and q" is an integer from 1 to 20.

Crosslinking agents and monofunctional monomeric compounds provide a physical framework, or gel, after crosslinking to host the polar aprotic solvent. Variation of the amount of the crosslinking agent and monofunctional monomeric compound in the gel may impact the conductivity of the gel electrolyte, due to changes in viscosity. Lower viscosity gels are prepared with higher concentrations of monofunctional monomeric compound, as compared to the concentration of monofunctional monomeric compound used for higher viscosity gels. Without being bound by theory, higher viscosity gels may be expected to have lower electrochemical conductivity, while lower viscosity gels may be expected to have higher electrochemical conductivity. However, other electrochemical properties of the gel electrolyte, or an electrochemical cell prepared with the gel electrolyte, such as oxidation potential and reduction potential, are not expected to be impacted.

Polymerization of crosslinking agents and monofunctional monomeric compounds are known to those of skill in the art. For example, monofunctional monomeric compounds may be polymerized by thermal and photo initiation. Representative thermal initiators include, but are not limited to, an azo compound, a peroxide compound, bismaleimide, or a mixture of any two or more thereof. One example of an azo compound is azoisobutyronitrile. One example of a peroxide compound is benzoylperoxide. Representative photoinitiators include, but are not limited to, 1-hydroxyl-phenyl-ketone, benzophenone, 2-hydroxyl-2-methyl-1-phenyl-propanone, 2-hydroxyl-1-[4-(2-hydroxy)phenyl]-2-methyl-1-propanone, methylbenzoylformate, oxy-phenyl-acetic acid 2-[2-oxo-2-phenyl-acetoxy-ethoxy]-ethyl ester, oxy-phenyl-acetic 2-[2-hydroxy-ethoxy]-ethyl ester, α,α-dimethoxy-α-phenylacetophenone, 2-benzyl-2-(dimethylamino)-1-[4-(4-morpholinyl)phenyl]-1-propanone, diphenyl (2,4,6-trimethylthio)phenyl)-phosphine oxide, phosphine oxide, phenyl bis(2,4,6-trimethyl benzoyl), bis($\eta^5$-2,4-cyclopentadien-1-yl) bis[2,6-difluoro-3-(1H-pyrrol-1-yl)phenyl]titanium, iodonium (4-methylphenyl)-[4-(2-methylpropyl)phenyl]-hexafluorophosphate, or a mixture of two or more thereof. In some instances the photoinitiator is a UV initiator.

In another aspect, a battery is provided including a plurality of series-connected rechargeable lithium ion cells. In such embodiments, each cell includes a negative electrode; a negative electrode current collector; a positive electrode; a positive electrode current collector; and an electrolyte as described above including the polar, aprotic solvent, the lithium salt, and the redox shuttle. In such systems the negative electrode has a larger irreversible first cycle capacity loss than that of the positive electrode, because the redox shuttle has an electrochemical potential above the positive electrode maximum normal operating potential, and the negative current collector has a lithium alloying potential below the negative electrode minimum normal operating potential. In one embodiment, the electrode balance is adjusted (by using a larger capacity negative electrode than positive electrode) so that the redox shuttle can provide overcharge protection as well.

A variety of negative electrodes may be employed in lithium-ion batteries. Representative negative electrodes include $Li_4Ti_5O_{12}$; the lithium alloy compositions described in U.S. Pat. Nos. 6,203,944; 6,255,017; 6,436,578; 6,664,004; and 6,699,336; U.S. Patent Application Publication Nos. 2003/0211390; 2004/013 1936; 2005/0031957; and 2006/046144; graphitic carbons e.g., those having a spacing between (002) crystallographic planes, $d_{002}$, of 3.45 Å>$d_{002}$>3.354 Å and existing in forms such as powders, flakes, fibers or spheres (e.g., mesocarbon microbeads (MCMB)); other materials that will be familiar to those skilled in the art; and combinations thereof.

Where the negative electrode has a larger irreversible first cycle capacity loss than that of the positive electrode, the positive electrode will normally remain at an elevated potential during over-discharge. Its current collector will be held near the same elevated potential and will not be susceptible to lithium capture during recharging or dissolution during over-discharging. Accordingly, there are fewer constraints on selection of the positive electrode current collector. Representative positive electrode current collectors include aluminum, stainless steels (e.g., 300 series and 400 series stainless steels), titanium, tantalum, niobium, INCONEL alloys, combinations thereof and other materials that will be familiar to those skilled in the art. A variety of positive electrodes may be employed in lithium-ion batteries in conjunction with the redox shuttles. Representative positive electrodes include $LiFePO_4$, $LiMnPO_4$, $LiMn_2O_4$, $LiCoPO_4$, and $LiCoO_2$; lithium transition metal oxides as disclosed in U.S. Pat. Nos.

5,858,324; 5,900,385; 6,143,268; 6,680,145; 6,964,828; 7,078,128; and 7,211,237; U.S. Patent Application Publication Nos. 2003/0027048; 2004/0121234; 2004/0 179993; and 2006/045144.

The negative or positive electrode may contain additives such as will be familiar to those skilled in the art, e.g., carbon black for negative electrodes, and carbon black, flake graphite and the like for positive electrodes.

The negative and positive electrode capacities may optionally be selected to provide an excess negative electrode capacity. This enables the redox shuttle to provide overcharge protection. Ten percent to twenty percent excess negative electrode capacity is recommended. Lesser or greater excess negative electrode capacities may be employed if desired.

In another aspect, an electrical device is provided including an electrical load (e.g., an electronic circuit, motor, illumination source or heat source) and the above-described battery. Exemplary embodiments of the recited device can be made without electronic over-discharge (and optionally without electronic overcharge) protection circuitry.

The following terms are used throughout as defined below.

The term "spinel" refers to manganese-based spinel such as, e.g., $Li_{1+x}Mn_{2-z}Met_yO_{4-m}X_n$, wherein Met is Al, Mg, Ti, B, Ga, Si, Ni, or Co; X is S or F; and wherein 0≤x≤0.3, 0≤y≤0.5, 0≤z≤0.5, 0≤m≤0.5 and 0≤n≤0.5.

The term "olivine" refers to iron-based olivine such as, e.g., $LiFe_{1-z}Met''_yPO_{4-m}X_n$, wherein Met" is Al, Mg, Ti, B, Ga, Si, Ni, Mn or Co; X is S or F; and wherein 0≤x≤0.3; 0≤y≤0.5, 0≤z≤0.5, 0≤m≤0.5 and 0≤n≤0.5.

Alkyl groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term haloalkyl is an alkyl group having one or more halo groups. In some embodiments, haloalkyl refers to a per-haloalkyl group.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to: 2,2-; 2,3-; 2,4-; 2,5-; or 2,6-disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

Alkenyl groups are straight chain, branched or cyclic alkyl groups having 2 to about 20 carbon atoms, and further including at least one double bond. In some embodiments alkenyl groups have from 1 to 12 carbons, or, typically, from 1 to 8 carbon atoms. Alkenyl groups include, for instance, vinyl, propenyl, 2-butenyl, 3-butenyl, isobutenyl, cyclohexenyl, cyclopentenyl, cyclohexadienyl, butadienyl, pentadienyl, and hexadienyl groups among others. Alkenyl groups may be substituted similarly to alkyl groups. Divalent alkenyl groups, i.e., alkenyl groups with two points of attachment, include, but are not limited to, $CH—CH{=}CH_2$, $C{=}CH_2$, or $C{=}CHCH_3$.

Alkynyl groups are straight chain or branched alkyl groups having 2 to about 20 carbon atoms, and further including at least one triple bond. In some embodiments alkynyl groups have from 1 to 12 carbons, or, typically, from 1 to 8 carbon atoms. Exemplary alkynyl groups include, but are not limited to, ethynyl, propynyl, and butynyl groups. Alkynyl groups may be substituted similarly to alkyl groups. Divalent alkynyl groups, i.e., alkynyl groups with two points of attachment, include but are not limited to $CH—C{\equiv}CH$.

One skilled in the art will readily realize that all ranges discussed can and do necessarily also describe all subranges therein for all purposes, and that all such subranges also form part and parcel of this disclosure. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology, thus generally described, will be understood more readily by reference to the following examples, which are provided by way of illustration and are not intended to be limiting.

EXAMPLES

Example 1

Synthesis of 1,4-bis(2-methoxyethoxy)-2,5-di-tert-butylbenzene. Scheme 1 is an illustration of the synthesis of the title compound.

Scheme 1:

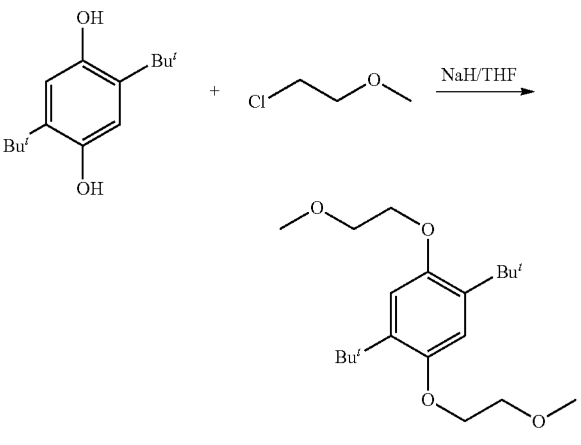

2,5-Di-tert-butylhydroquinone (0.2 mmol) was dissolved in anhydrous THF (20 ml). Sodium hydride (0.6 mmol) and 2-chloroethylethylether (0.4 mmol) was then added to the solution. The reaction mixture was then stirred at room temperature overnight. After removal of the solvent, the residue was partitioned between dichloromethane and aqueous $NaHCO_3$ (0.1M). The organic portion was separated and dried over $Na_2SO_4$. After solvent removal in vacuo, the crude product was chromatographed (silica, hexanes/DCM from 5:1 to 1:1) to afford 1,4-bis(2-methoxyethoxy)-2,5-di-tert-butyl-benzene in an 81% yield. The product was characterized by $^1H$ NMR (300 MHz, $CDCl_3$, δ/ppm): 7.14 (s, 2H), 4.11 (t, J=4.5 Hz, 4H), 3.80 (t, J=4.5 Hz, 4H), 3.45 (s, 6H), 1.37 (s, 18H).

Example 2

Synthesis of 1,4-bis[(2-methoxyethoxy)methoxy]-2,5-di-tert-butyl-benzene. The title compound was prepared in a manner similar to that of Example 1, by dissolving 2,5-Di-tert-butylhydroquinone (0.2 mmol) in anhydrous THF (20 ml). Sodium hydride (0.6 mmol) and 2-methoxyethoxymethyl chloride (0.4 mmol) was added to the solution. The reaction was stirred at room temperature overnight. After removal the solvent, the residue was partitioned between dichloromethane and aqueous $NaHCO_3$ (0.1M). The organic portion was separated and dried over $Na_2SO_4$. After solvent removal in vacuo, the crude product was chromatographed (silica, hexanes/DCM from 5:1 to 1:1) to afford 1,4-bis[(2-methoxyethoxy)methoxy]-2,5-di-tert-butyl-benzene in an 80% yield. The product was characterized by $^1H$ NMR (300 MHz, $CDCl_3$, δ/ppm): 7.14 (s, 2H), 5.25 (s, 4H), 3.85 (t, J=4.5 Hz, 4H), 3.61 (t, J=4.5 Hz, 4H), 3.40 (s, 6H), 1.36 (s, 18H).

Example 3

Cyclic voltammograms were recorded for a solution of 1,4-bis(2-methoxyethoxy)-2,5-di-tert-butyl-benzene (10 mM) as a redox shuttle in 1.2 M $LiPF_6$ in EC/EMC (3:7 by weight) using a three electrode system (Pt working electrode, Li counter electrode, and Li reference electrode) at different scan rates. See FIG. 1. One pair of reversible peaks is observed 3.8-4.1V vs. $Li/Li^+$. The main electrolyte components (EC, PC, DMC, and $LiPF_6$) are electrochemically stable up to 4.8 V vs. $Li/Li^+$, or higher. The reversible electrochemical reaction at 3.8-4.1 V vs. $Li/Li^+$ is thus assigned to the reduction and oxidation peaks for the 1,4-bis(2-methoxyethoxy)-2,5-di-tert-butyl-benzene.

Example 4

Figure 2:
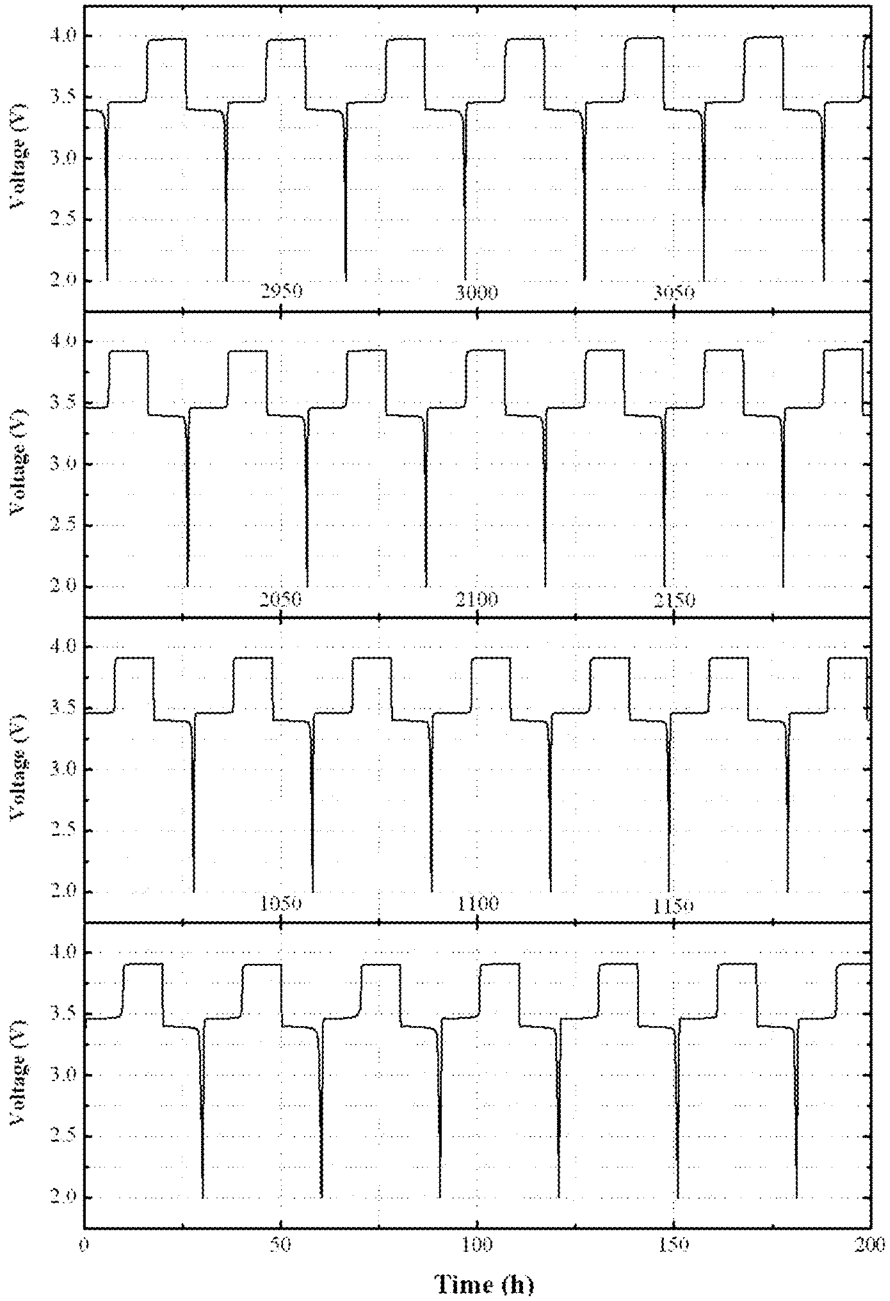
FIG. 2 is a series of voltage profiles for a $Li/LiFePO_4$ cell containing 0.1M 1,4-Bis(2-methoxyethoxy)-2,5-di-tert-butyl-benzene in 1.2M $LiPF_6$ in EC/EMC (3:7 by weight) during the course of 0 h to 3100 h at a charging rate of C/10, and overcharge of 100%.

Voltage profiles of a $Li/LiFePO_4$ cell containing 0.1M 1,4-bis(2-methoxyethoxy)-2,5-di-tert-butyl-benzene as a redox shuttle in 1.2M $LiPF_6$ in EC/EMC (3:7 by weight) were recorded over the course of 0 h to 3100 h. See FIG. 2. The charging rate was at C/10 and the overcharge is 100%. The redox shuttle shows excellent overcharge protection performance in the conventional carbonate-based electrolyte, and even at 0.1 M no solubility issues are observed.

Example 5

Figure 3:
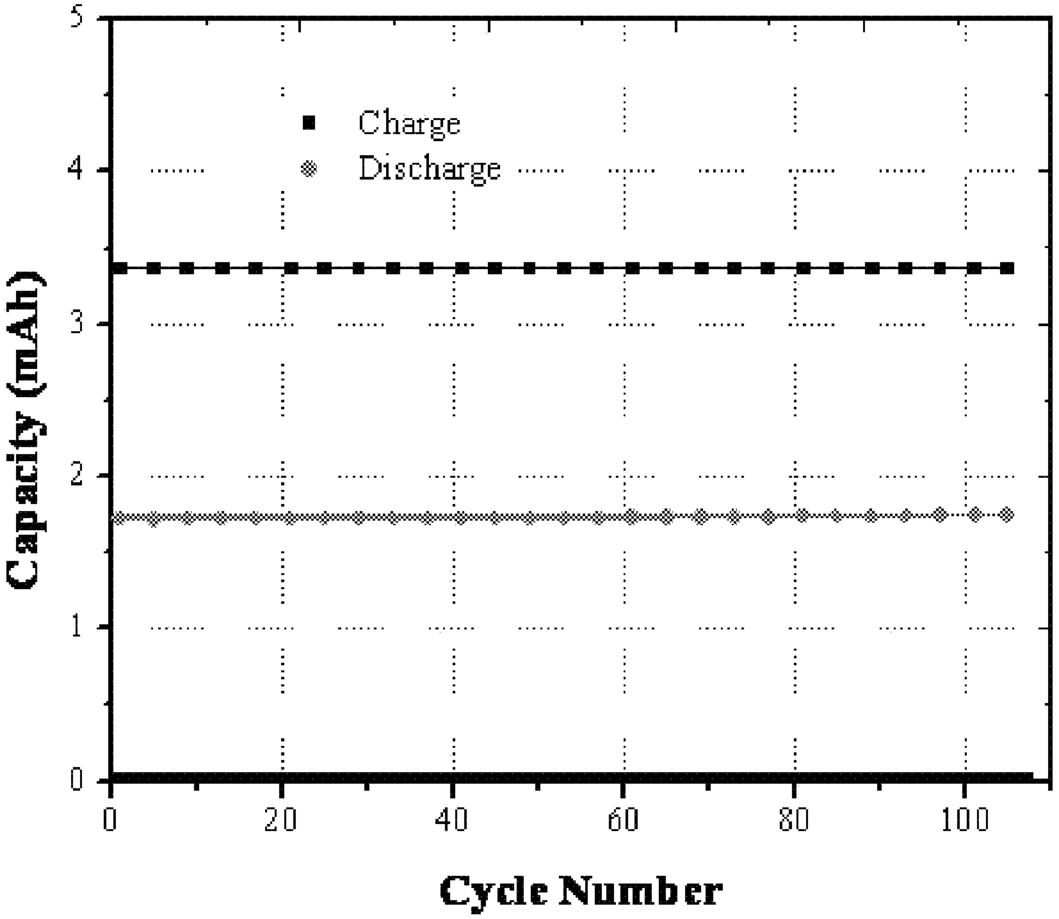
FIG. 3 is a capacity retention profile for a $Li/LiFePO_4$ cell containing 0.1M 1,4-bis(2-methoxyethoxy)-2,5-di-tert-butyl-benzene in 1.2M $LiPF_6$ in EC/EMC (3:7 by weight) during the course of 0 h to 3100 h at a charging rate of C/10, and overcharge is 100%.

Capacity retention profiles of $Li/LiFePO_4$ cell containing 0.1 M 1,4-Bis(2-methoxyethoxy)-2,5-di-tert-butyl-benzene in 1.2M $LiPF_6$ in EC/EMC (3:7 by weight) were recorded over the course of 0 h to 3100 h. See FIG. 3 The charging rate was at C/10 and the overcharge is 100%. After more than one hundred overcharge cycles, the cell performance in regards of capacity retention does exhibit an obvious decrease.

Example 6

Figure 4:
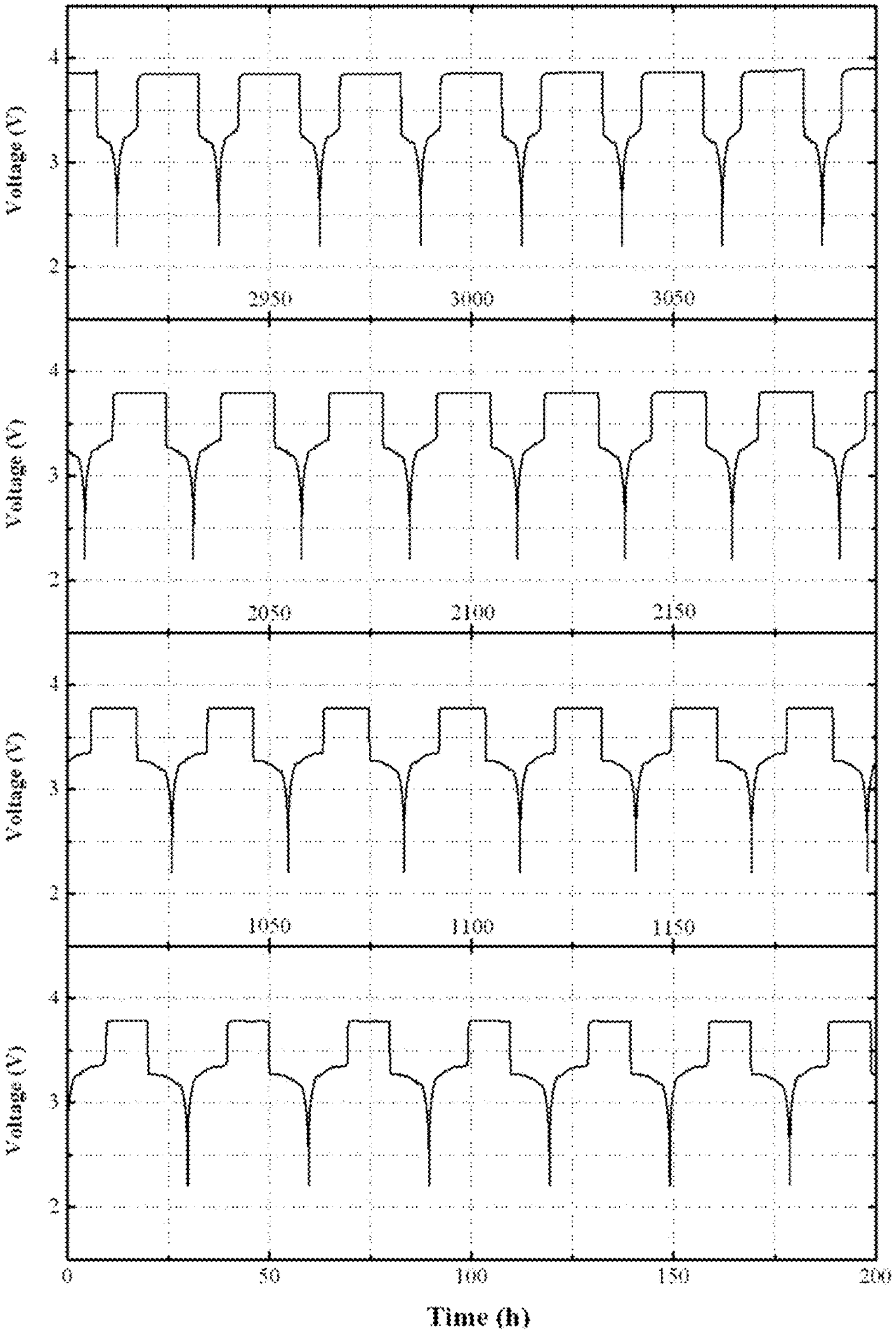
FIG. 4 is a series of voltage profiles for a $MCMB/LiFePO_4$ cell containing 0.1M 1,4-bis(2-methoxyethoxy)-2,5-di-tert-butyl-benzene in 1.2M $LiPF_6$ in EC/EMC (3:7 by weight) during the course of 0 h to 3100 h at a charging rate of C/10, and overcharge is 100%.

Voltage profiles of a $MCMB/LiFePO_4$ cell containing 0.1 M 1,4-bis(2-methoxyethoxy)-2,5-di-tert-butyl-benzene as a redox shuttle in 1.2M $LiPF_6$ in EC/EMC (3:7 by weight) were recorded over the course of 0 h to 3100 h. See FIG. 4. The charging rate was at C/10 and the overcharge is 100%. The overcharge protection resulted from the exemplary redox shuttle works well in the full cell with MCMB as the anode. As used herein, MCMB is an abbreviation for mesocarbon microbeads.

Example 7

Figure 5:
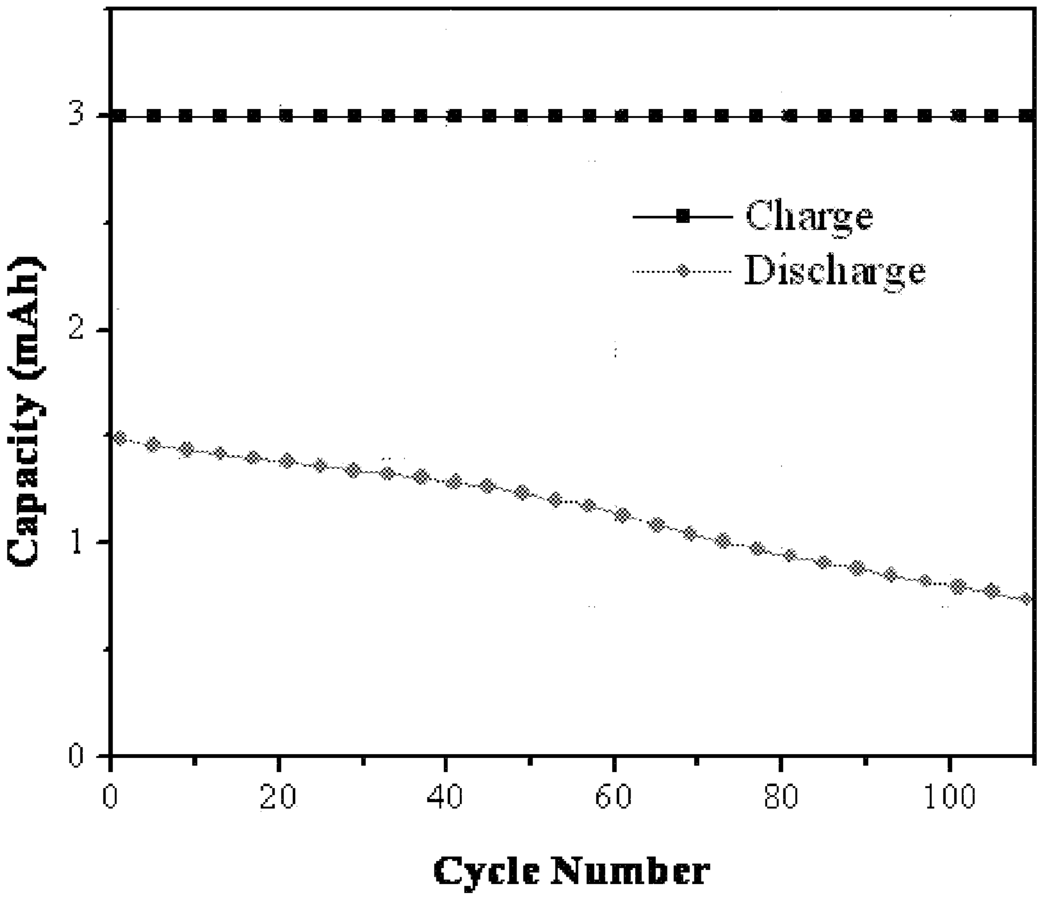
FIG. 5 is a capacity retention profile for a $MCMB/LiFePO_4$ cell containing 0.1M 1,4-bis(2-methoxyethoxy)-2,5-di-tert-butyl-benzene in 1.2M $LiPF_6$ in EC/EMC (3:7 by weight) during the course of 0 h to 3100 h, at a charging rate of C/10, and overcharge is 100%.

Capacity retention profiles of $MCMB/LiFePO_4$ cell containing 0.1 M 1,4-Bis(2-methoxyethoxy)-2,5-di-tert-butyl-benzene in 1.2M $LiPF_6$ in EC/EMC (3:7 by weight) were recorded over the course of 0 h to 3100 h. See FIG. 5. The charging rate was at C/10 and the overcharge is 100%. After one hundred overcharge cycles, the discharge capacities of the test cells decreased by approximately 30%. It is believed that the high voltage overcharge tests are beyond the normal working range of the cells, thus leading to degradation.

Example 8

Figure 6:
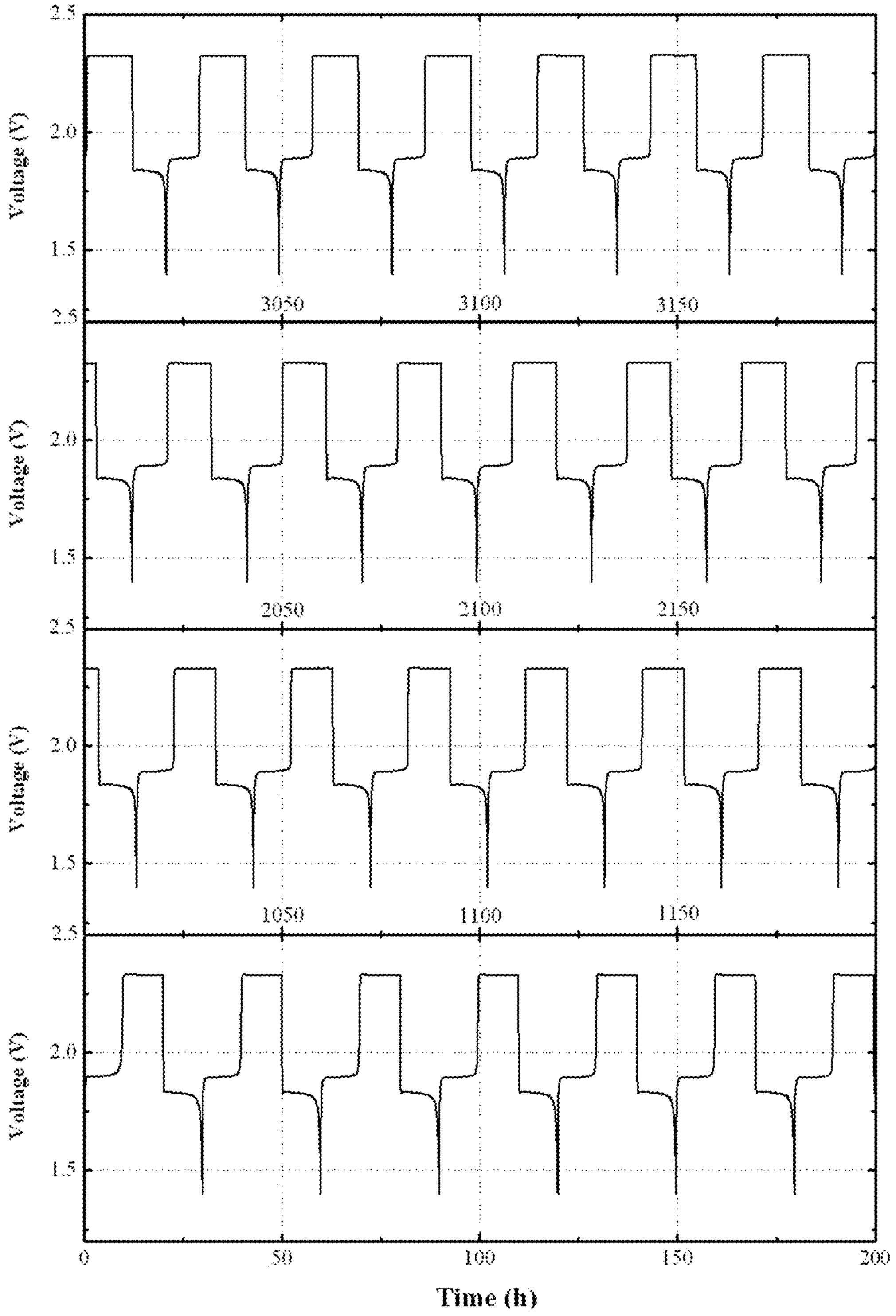
FIG. 6 is a series of voltage profiles for a $LTO/LiFePO_4$ cell containing 0.1M 1,4-bis(2-methoxyethoxy)-2,5-di-tert-butyl-benzene in 1.2M $LiPF_6$ in EC/EMC (3:7 by weight) during the course of 0 h to 3100 h at a charging rate of C/10, and overcharge is 100%.

Voltage profiles of a $LTO/LiFePO_4$ cell containing 0.1 M 1,4-bis(2-methoxyethoxy)-2,5-di-tert-butyl-benzene as a redox shuttle in 1.2M $LiPF_6$ in EC/EMC (3:7 by weight) were recorded over the course of 0 h to 3100 h. See FIG. 6. The charging rate was at C/10 and the overcharge is 100%. The overcharge protection works well in full cells with LTO as anode for more than 100 overcharge cycles. As used herein, LTO is an abbreviation for lithium titanium oxide.

Example 9

Figure 7:
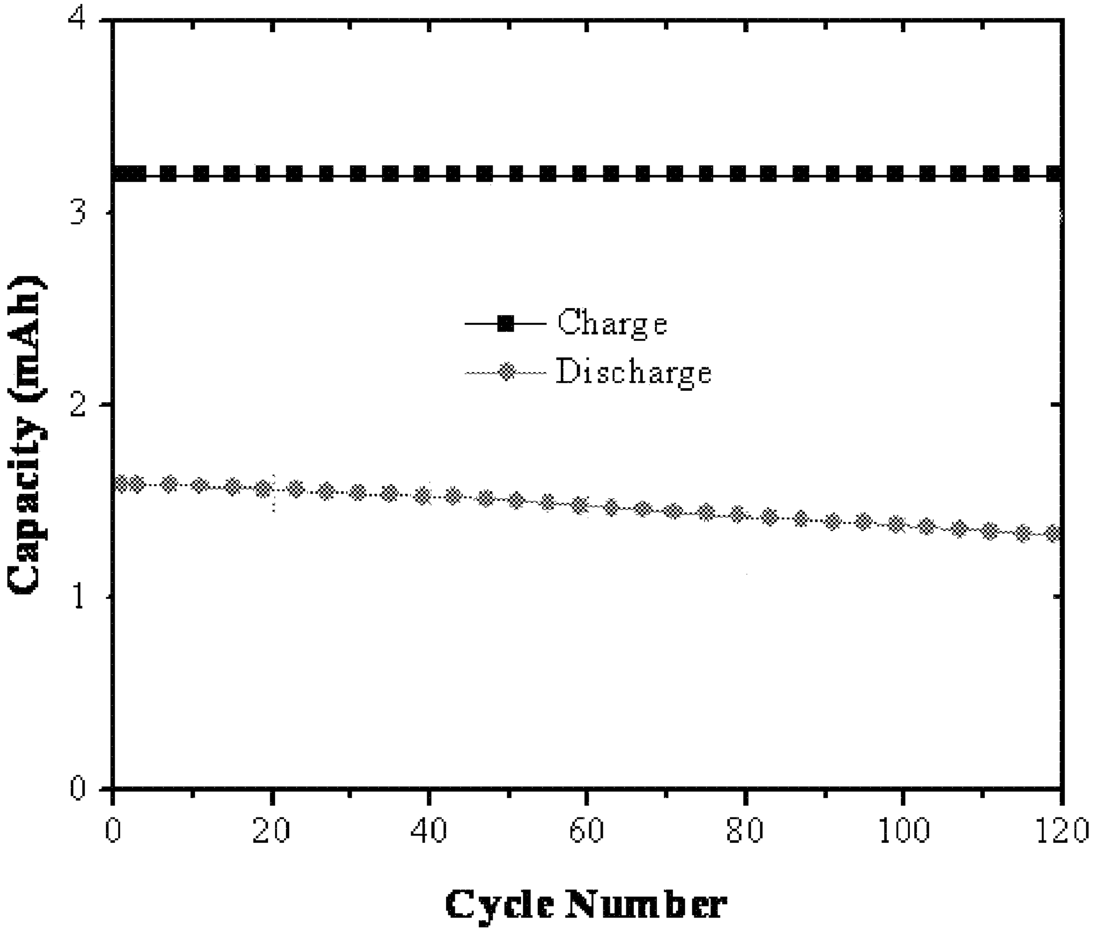
FIG. 7 is a capacity retention profile for a $LTO/LiFePO_4$ cell containing 0.1M 1,4-bis(2-methoxyethoxy)-2,5-di-tert-butyl-benzene in 1.2M $LiPF_6$ in EC/EMC (3:7 by weight) during the course of 0 h to 3100 h, at a charging rate of C/10, and overcharge is 100%.

Capacity retention profiles of $LTO/LiFePO_4$ cell containing 0.1 M 1,4-Bis(2-methoxyethoxy)-2,5-di-tert-butyl-benzene in 1.2M $LiPF_6$ in EC/EMC (3:7 by weight) were recorded over the course of 0 h to 3100 h. See FIG. 7. The charging rate was at C/10 and the overcharge is 100%. After one hundred overcharge cycles, the discharge capacities of the test cells decreased by approximately 10%.

Example 10

Figure 8:
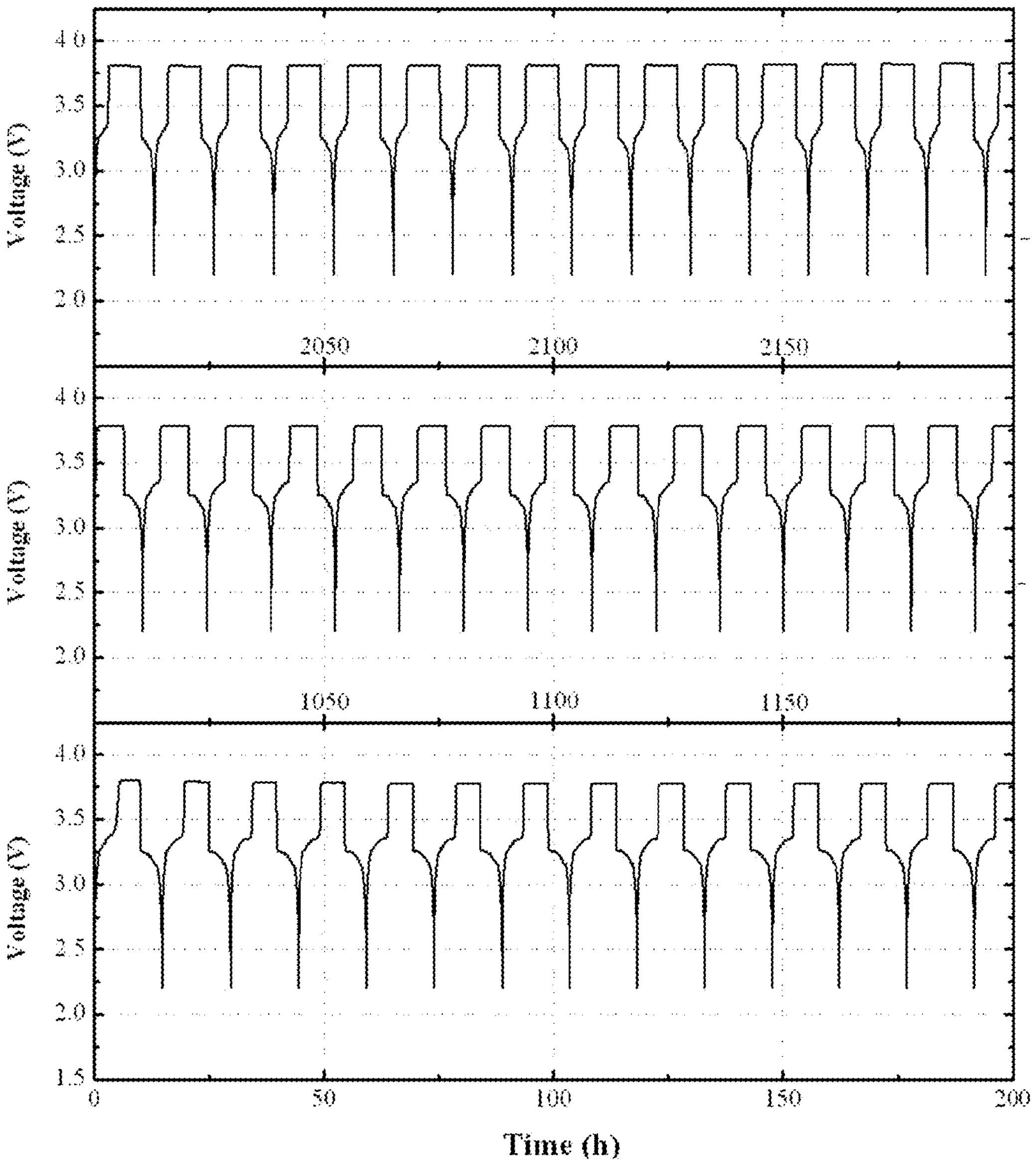
FIG. 8 is a series of voltage profiles for a $MCMB/LiFePO_4$ cell containing 0.2 M 1,4-bis(2-methoxyethoxy)-2,5-di-tert-butyl-benzene in 1.2M $LiPF_6$ in EC/EMC (3:7 by weight) during the course of 0 h to 3100 h at a charging rate of C/5, and overcharge is 100%.

Voltage profiles of a $MCMB/LiFePO_4$ cell containing 0.2 M 1,4-bis(2-methoxyethoxy)-2,5-di-tert-butyl-benzene as a redox shuttle in 1.2M $LiPF_6$ in EC/EMC (3:7 by weight) were recorded over the course of 0 h to 3100 h. See FIG. 8. The charging rate was at C/10 and the overcharge is 100%. The redox shuttle shows excellent solubility in carbonate-based electrolytes, which in return benefits the overcharge performance. The full cells containing 0.2 M redox shuttle displayed superior overcharge protection. Due to the relative high concentration of redox shuttle, the cells are expected to provide thousands of hours overcharge protection at a C/5 charging rate.

Example 11

Figure 9:
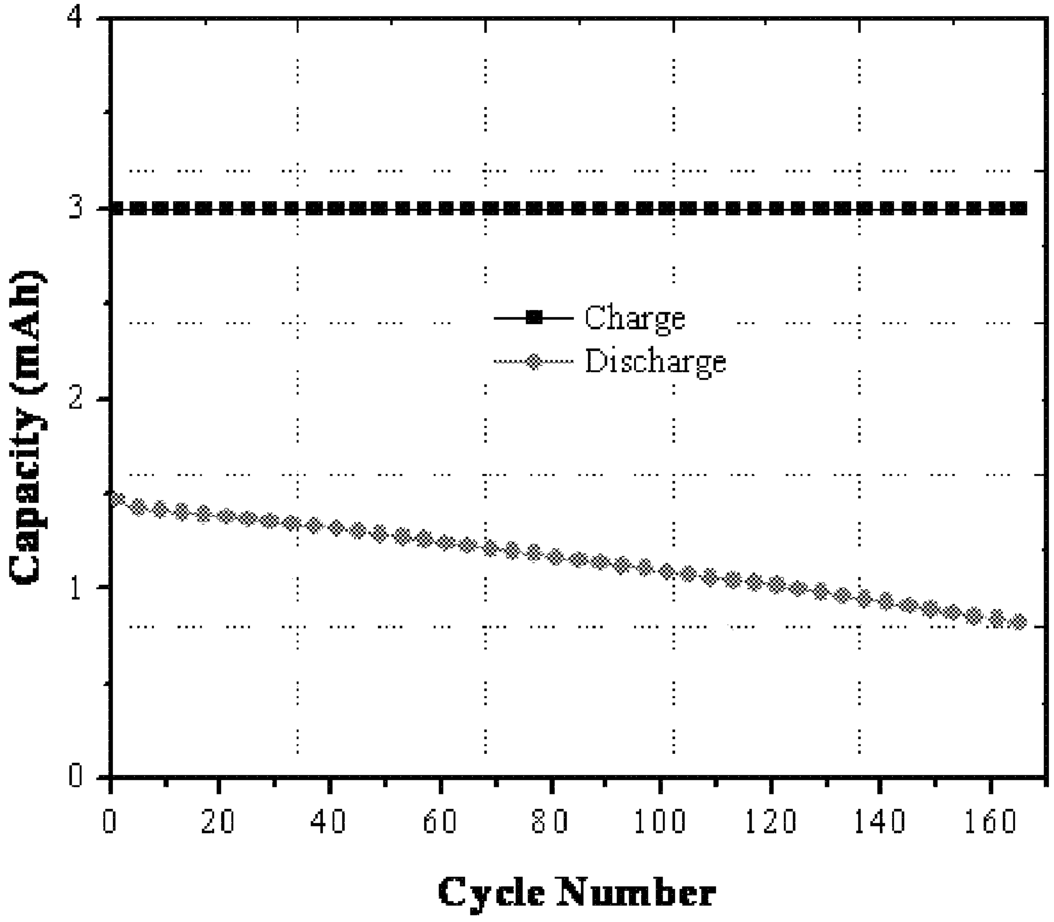
FIG. 9 is a capacity retention profile for a $MCMB/LiFePO_4$ cell containing 0.2 M 1,4-bis(2-methoxyethoxy)-2,5-di-tert-butyl-benzene in 1.2M $LiPF_6$ in EC/EMC (3:7 by weight) during the course of 0 h to 3100 h, at a charging rate of C/5, and overcharge is 100%.

Capacity retention profiles of $MCMB/LiFePO_4$ cell containing 0.2 M 1,4-Bis(2-methoxyethoxy)-2,5-di-tert-butylbenzene in 1.2M $LiPF_6$ in EC/EMC (3:7 by weight) were recorded over the course of 0 h to 3100 h. See FIG. 9. The charging rate was at C/10 and the overcharge is 100%. After more than 160 overcharge cycles at C/5 rate, the cells still work properly despite the decrease in the discharge capacity.

Example 12

Figure 10:
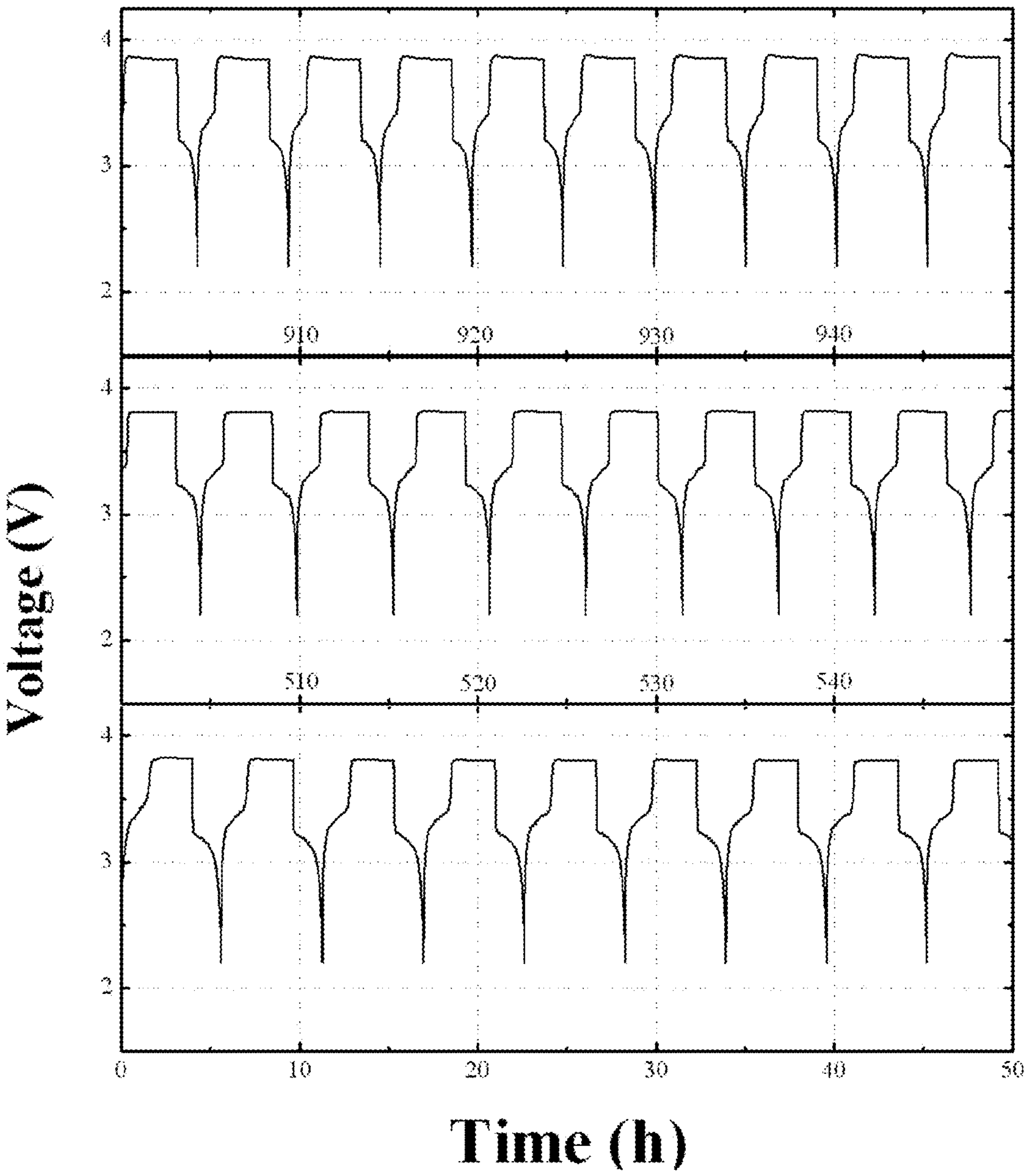
FIG. 10 is a series of voltage profiles for a $MCMB/LiFePO_4$ cell containing 0.4 M 1,4-bis(2-methoxyethoxy)-2,5-di-tert-butyl-benzene in 1.2M $LiPF_6$ in EC/EMC (3:7 by weight) during the course of 0 h to 3100 h at a charging rate of C/2, and overcharge is 100%.

Voltage profiles of a MCMB/$LiFePO_4$ cell containing 0.4 M 1,4-bis(2-methoxyethoxy)-2,5-di-tert-butyl-benzene as a redox shuttle in 1.2M $LiPF_6$ in EC/EMC (3:7 by weight) were recorded over the course of 0 h to 3100 h. See FIG. 10. The charging rate was at C/10 and the overcharge is 100%. The improved solubility of the exemplary redox shuttle compound made it possible to use this redox compound under C/2 rate. The cells containing 0.4 M current redox shuttle compound can provide more than one thousand hours overcharge protection under a C/2 rate.

Example 11

Figure 11:
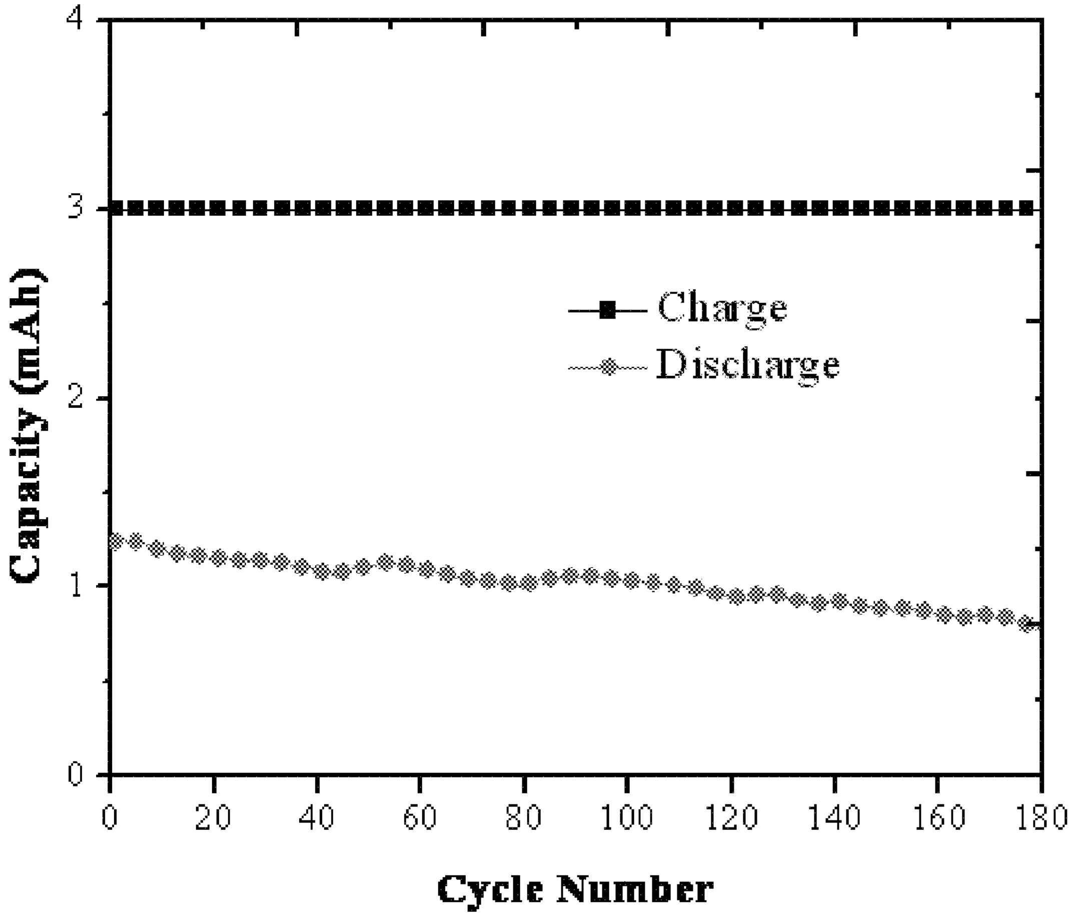
FIG. 11 is a capacity retention profile for a $MCMB/LiFePO_4$ cell containing 0.4 M 1,4-bis(2-methoxyethoxy)-2,5-di-tert-butyl-benzene in 1.2M $LiPF_6$ in EC/EMC (3:7 by weight) during the course of 0 h to 3100 h, at a charging rate of C/2, and overcharge is 100%.

Capacity retention profiles of MCMB/$LiFePO_4$ cell containing 0.4 M 1,4-Bis(2-methoxyethoxy)-2,5-di-tert-butyl-benzene in 1.2M $LiPF_6$ in EC/EMC (3:7 by weight) were recorded over the course of 0 h to 3100 h. See FIG. 11. The charging rate was at C/10 and the overcharge is 100%. After more than 180 overcharge cycles at C/2 rate, the cells still work properly despite the decrease in the discharge capacity.

We claim:

1. A compound represented by Formula I, II, or III:

I

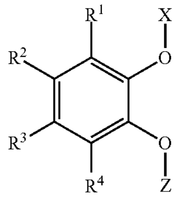

II

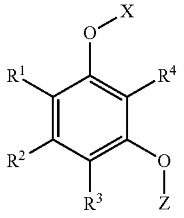

III

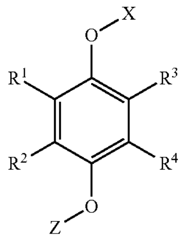

wherein:

$R^1$ is n-propyl, iso-propyl, n-butyl, sec-butyl, or tert-butyl;

$R^2$ is H, F, Cl, Br, CN, $NO_2$, alkyl, haloalkyl, phosphate, or polyether, or $R^1$ and $R^2$ join together to form a ring;

$R^3$ is H, F, Cl, Br, CN, $NO_2$, alkyl, haloalkyl, phosphate, or polyether; or where the compound is represented by Formula II, $R^1$ and $R^2$, or $R^2$ and $R^3$ join together to form a ring;

$R^4$ is n-propyl, iso-propyl, n-butyl, sec-butyl, or tert-butyl; and

X and Z are independently a group of Formula A:

A

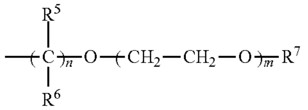

wherein:

$R^5$ and $R^6$ are independently H, F, Cl, Br, CN, $NO_2$, alkyl, haloalkyl, phosphate, or polyether;

$R^7$ is alkyl, haloalkyl, phosphate, or polyether;

n is an integer from 1 to 8; and m is an integer from 1 to 13.

2. The compound of claim 1, wherein $R^2$ and $R^3$ are hydrogen.

3. The compound of claim 1 represented by Formula I.

4. The compound of claim 3, wherein:

$R^2$ and $R^3$ are independently H, $C_1$-$C_4$ alkyl, $C_1$-$C_4$ haloalkyl, or a polyether group having from 2 to 20 carbon atoms;

$R^5$ and $R^6$ at each occurrence are individually H, a $C_1$-$C_4$ alkyl, a $C_1$-$C_4$ haloalkyl, H, Cl, Br, or I;

$R^7$ is alkyl;

n is 1 or 2; and m is 1 to 8.

5. The compound of claim 1 represented by Formula II.

6. The compound of claim 1 represented by Formula III.

7. The compound of claim 6, wherein:

$R^1$ and $R^4$ are tert-butyl;

$R^2$ and $R^3$ are H;

$R^5$ and $R^6$ at each occurrence are individually H or methyl;

$R^7$ is methyl, or ethyl;

n is 1 or 2; and m is 1 to 8.

8. The compound of claim 1, wherein $R^7$ is $C_1$-$C_4$ alkyl.

9. A compound which is 1,4-bis(2-(2-methoxy)ethoxy)ethoxy-2,5-di-tert-butyl-benzene; 1,4-bis(2-(2-(2-methoxy)ethoxy)ethoxy)ethoxy-2,5-di-tert-butyl-benzene; or 1,4-bis(2-(2-(2-(2-methoxy)ethoxy)ethoxy)ethoxy)ethoxy-2,5-di-tert-butyl-benzene.

10. An electrolyte comprising:

an alkali metal salt;

a polar aprotic solvent; and a redox shuttle comprising a compound represented by Formula I, II, or III:

I

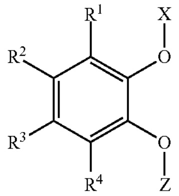

-continued

II

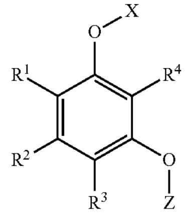

III

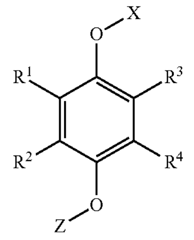

wherein:

$R^1$ is H, F, Cl, Br, CN, $NO_2$, alkyl, haloalkyl, phosphate, or polyether;

$R^2$ is H, F, Cl, Br, CN, $NO_2$, alkyl, haloalkyl, phosphate, or polyether, or $R^1$ and $R^2$ join together to form a ring;

$R^3$ is H, F, Cl, Br, CN, $NO_2$, alkyl, haloalkyl, phosphate, or polyether; or where the compound is represented by Formula II, $R^1$ and $R^2$, or $R^2$ and $R^3$ join together to form a ring;

$R^4$ is H, F, Cl, Br, CN, $NO_2$, alkyl, haloalkyl, phosphate, or polyether; or $R^3$ and $R^4$ join together to form a ring; and X and Z are independently a group of Formula A:

A

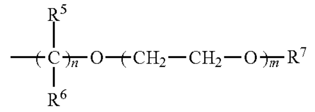

wherein:

$R^5$ and $R^6$ are independently H, F, Cl, Br, CN, $NO_2$, alkyl, haloalkyl, phosphate, or polyether;

$R^7$ is H, alkyl, haloalkyl, phosphate, or polyether;

n is an integer from 1 to 8;

m is an integer from 1 to 13; and wherein the electrolyte solution is substantially non-aqueous.

11. An electrochemical device comprising a cathode an anode; and a substantially non-aqueous electrolyte comprising:

an alkali metal salt;

a polar aprotic solvent; and a compound represented by Formula I, II, or III;

wherein:

Formula I, II, and III are:

I

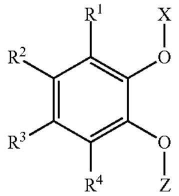

II

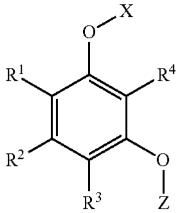

III

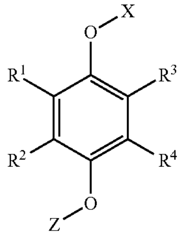

$R^1$ is H, F, Cl, Br, CN, $NO_2$, alkyl, haloalkyl, phosphate, or polyether;

$R^2$ is H, F, Cl, Br, CN, $NO_2$, alkyl, haloalkyl, phosphate, or polyether, or $R^1$ and $R^2$ join together to form a ring;

$R^3$ is H, F, Cl, Br, CN, $NO_2$, alkyl, haloalkyl, phosphate, or polyether; or where the compound is represented by Formula II, $R^1$ and $R^2$, or $R^2$ and $R^3$ join together to form a ring;

$R^4$ is H, F, Cl, Br, CN, $NO_2$, alkyl, haloalkyl, phosphate, or polyether; or $R^3$ and $R^4$ join together to form a ring; and X and Z are independently a group of Formula A:

A

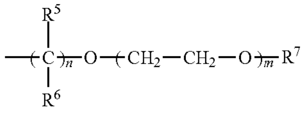

$R^5$ and $R^6$ are independently H, F, Cl, Br, CN, $NO_2$, alkyl, haloalkyl, phosphate, or polyether;

$R^7$ is H, alkyl, haloalkyl, phosphate, or polyether;

n is an integer from 1 to 8; and m is an integer from 1 to 13.

12. The electrolyte of claim 10, wherein $R^1$, $R^2$, $R^3$, and $R^4$ are independently H, $C_1$-$C_4$ alkyl, $C_1$-$C_4$ haloalkyl, or a polyether having from 2 to 20 carbon atoms.

13. The electrolyte of claim 10, wherein $R^1$ and $R^4$ are individually H, alkyl or haloalkyl, and $R^2$ and $R^3$ are hydrogen.

14. The electrolyte of claim 10, wherein $R^1$ and $R^4$ are individually H, methyl, ethyl, n-propyl, iso-propyl, n-butyl, sec-butyl, or tert-butyl, and $R^2$ and $R^3$ are H.

15. The electrolyte of claim 10 represented by Formula III.

16. The electrolyte of claim 15, wherein:

$R^1$ and $R^4$ are individually H, alkyl or haloalkyl;

$R^2$ and $R^3$ are hydrogen;

$R^5$ and $R^6$ at each occurrence are individually H or methyl;

$R^7$ is H, methyl, ethyl, n-propyl, iso-propyl, n-butyl, sec-butyl, or tert-butyl;

n is 1 or 2;

m is 1 to 8.

17. The electrolyte of claim 15, wherein:

$R^1$ and $R^4$ are tert-butyl;

$R^2$ and $R^3$ are H;

$R^5$ and $R^6$ at each occurrence are individually H or methyl;

$R^7$ is H, methyl, or ethyl;

n is 1 or 2; and m is 1 to 8.

18. The electrolyte of claim 10, wherein the compound is 1-nitro-3-tert-butyl-2,5-di-oligo(ethylene glycol)benzene; 1-cyano-3-tert-butyl-2,5-di-oligo(ethylene glycol)benzene; 1,4-di-tert-butyl-2,3-di-oligo(ethylene glycol)benzene; 5-tert-butyl-1,3-dinitro-2,4-di-oligo(ethylene glycol)benzene; 1-(benzyloxy)-4-bromo-2,3-di-oligo(ethylene glycol)benzene; 1,3,5-tri-tert-butyl-2,4-di-oligo(ethylene glycol)benzene; 2-methyl-1,4-di-oligo(ethylene glycol)benzene; 2,3-dimethyl-1,4-di-oligo(ethylene glycol)benzene; 2,5-dimethyl-1,4-di-oligo(ethylene glycol)benzene; 2,6-dimethyl-1,4-di-oligo(ethylene glycol)benzene; 2,3,6-trimethyl-1,2-di-oligo(ethylene glycol)benzene; 2,3,5,6-tetramethyl-1,4-di-oligo(ethylene glycol)benzene; 4-methyl-1,2-di-oligo(ethylene glycol)benzene; 2-ethyl-1,4-di-oligo(ethylene glycol)benzene; 2,3-diethyl-1,4-di-oligo(ethylene glycol)benzene; 2,5-diethyl-1,4-di-oligo(ethylene glycol)benzene; 2,6-diethyl-1,4-di-oligo(ethylene glycol)benzene; 2,3,6-triethyl-1,2-di-oligo(ethylene glycol)benzene; 2,3,5,6-tetraethyl-1,4-di-oligo(ethylene glycol)benzene; 4-ethyl-1,2-di-oligo(ethylene glycol)benzene; 2,5-diisopropyl-1,4-di-oligo(ethylene glycol)benzene; 2-tert-butyl-1,4-di-oligo(ethylene glycol)benzene; 2,3-di-tert-butyl-1,4-di-oligo(ethylene glycol)benzene; 2,5-di-tert-butyl-1,4-di-oligo(ethylene glycol)benzene; 2,5-di-tert-pentyl-1,4-di-oligo(ethylene glycol)benzene; 2,5-di-tert-butyl-3,6-di-nitro-1,4-di-oligo(ethylene glycol)benzene; 2,5-di-tert-butyl-3,6-di-cyano-1,4-di-oligo(ethylene glycol)benzene; 2,5-di-tert-butyl-1,4-di-oligo(ethylene glycol)benzene; 2,5-dicyclohexyl-1,4-di-oligo(ethylene glycol)benzene; 4-tert-butyl-1,2-di-oligo(ethylene glycol)benzene; 4,5-di-tert-butyl-1,2-di-oligo(ethylene glycol)benzene; 4,5-di-tert-pentyl-1,2-di-oligo(ethylene glycol)benzene; 4,5-di-tert-butyl-1,2-diethoxybenzene; 9,10-di-oligo(ethylene glycol)-1,4:5,8-dimethano-1,2,3,4,5,6,7,8-octahydroanthracene; 9,10-di-oligo(ethylene glycol)-1,4:5,8-diethano-1,2,3,4,5,6,7,8-octahydroanthracene; 1,4-bis(2-(2-methoxy)ethoxy)ethoxy-2,5-di-tert-butyl-benzene; 1,4-bis(2-(2-(2-methoxy)ethoxy)ethoxy)ethoxy-2,5-di-tert-butyl-benzene; or 1,4-bis(2-(2-(2-(2-methoxy)ethoxy)ethoxy)ethoxy)ethoxy-2,5-di-tert-butyl-benzene.

19. The electrolyte of claim 10, wherein the compound is 1,4-bis(2-(2-methoxy)ethoxy)ethoxy-2,5-di-tert-butyl-benzene; 1,4-bis(2-(2-(2-methoxy)ethoxy)ethoxy)ethoxy-2,5-di-tert-butyl-benzene; or 1,4-bis(2-(2-(2-(2-methoxy)ethoxy)ethoxy)ethoxy)ethoxy-2,5-di-tert-butyl-benzene.

20. The electrochemical device of claim 11, wherein the compound is 1-nitro-3-tert-butyl-2,5-di-oligo(ethylene glycol)benzene; 1-cyano-3-tert-butyl-2,5-di-oligo(ethylene glycol)benzene; 1,4-di-tert-butyl-2,3-di-oligo(ethylene glycol)benzene; 5-tert-butyl-1,3-dinitro-2,4-di-oligo(ethylene glycol)benzene; 1-(benzyloxy)-4-bromo-2,3-di-oligo(ethylene glycol)benzene; 1,3,5-tri-tert-butyl-2,4-di-oligo(ethylene glycol)benzene; 2-methyl-1,4-di-oligo(ethylene glycol)benzene; 2,3-dimethyl-1,4-di-oligo(ethylene glycol)benzene; 2,5-dimethyl-1,4-di-oligo(ethylene glycol)benzene; 2,6-dimethyl-1,4-di-oligo(ethylene glycol)benzene; 2,3,6-trimethyl-1,2-di-oligo(ethylene glycol)benzene; 2,3,5,6-tetramethyl-1,4-di-oligo(ethylene glycol)benzene; 4-methyl-1,2-di-oligo(ethylene glycol)benzene; 2-ethyl-1,4-di-oligo(ethylene glycol)benzene; 2,3-diethyl-1,4-di-oligo(ethylene glycol)benzene; 2,5-diethyl-1,4-di-oligo(ethylene glycol)benzene; 2,6-diethyl-1,4-di-oligo(ethylene glycol)benzene; 2,3,6-triethyl-1,2-di-oligo(ethylene glycol)benzene; 2,3,5,6-tetraethyl-1,4-di-oligo(ethylene glycol)benzene; 4-ethyl-1,2-di-oligo(ethylene glycol)benzene; 2,5-diisopropyl-1,4-di-oligo(ethylene glycol)benzene; 2-tert-butyl-1,4-di-oligo(ethylene glycol)benzene; 2,3-di-tert-butyl-1,4-di-oligo(ethylene glycol)benzene; 2,5-di-tert-butyl-1,4-di-oligo(ethylene glycol)benzene; 2,5-di-tert-pentyl-1,4-di-oligo(ethylene glycol)benzene; 2,5-di-tert-butyl-3,6-di-nitro-1,4-di-oligo(ethylene glycol)benzene; 2,5-di-tert-butyl-3,6-di-cyano-1,4-di-oligo(ethylene glycol)benzene; 2,5-di-tert-butyl-1,4-di-oligo(ethylene glycol)benzene; 2,5-dicyclohexyl-1,4-di-oligo(ethylene glycol)benzene; 4-tert-butyl-1,2-di-oligo(ethylene glycol)benzene; 4,5-di-tert-butyl-1,2-di-oligo(ethylene glycol)benzene; 4,5-di-tert-pentyl-1,2-di-oligo(ethylene glycol)benzene; 4,5-di-tert-butyl-1,2-diethoxybenzene; 9,10-di-oligo(ethylene glycol)-1,4:5,8-dimethano-1,2,3,4,5,6,7,8-octahydroanthracene; 9,10-di-oligo(ethylene glycol)-1,4:5,8-diethano-1,2,3,4,5,6,7,8-octahydroanthracene; 1,4-bis(2-(2-methoxy)ethoxy)ethoxy-2,5-di-tert-butyl-benzene; 1,4-bis(2-(2-(2-methoxy)ethoxy)ethoxy)ethoxy-2,5-di-tert-butyl-benzene; or 1,4-bis(2-(2-(2-(2-methoxy)ethoxy)ethoxy)ethoxy)ethoxy-2,5-di-tert-butyl-benzene.

21. The electrochemical device of claim 11, wherein the compound is 1,4-bis(2-(2-methoxy)ethoxy)ethoxy-2,5-di-tert-butyl-benzene; 1,4-bis(2-(2-(2-methoxy)ethoxy)ethoxy)ethoxy-2,5-di-tert-butyl-benzene; or 1,4-bis(2-(2-(2-(2-methoxy)ethoxy)ethoxy)ethoxy)ethoxy-2,5-di-tert-butyl-benzene.

* * * * *